United States Patent
Coffman et al.

(10) Patent No.: US 9,428,546 B2
(45) Date of Patent: Aug. 30, 2016

(54) TANDEM PURIFICATION OF PROTEINS

(75) Inventors: Jonathan Lee Coffman, Union City, CA (US); Ranganathan Godavarti, Burlington, MA (US); Michael Shamashkin, Woburn, MA (US)

(73) Assignee: Pfizer Inc., New York, NY (US)

( * ) Notice: Subject to any disclaimer, the term of this patent is extended or adjusted under 35 U.S.C. 154(b) by 526 days.

(21) Appl. No.: 13/811,178

(22) PCT Filed: Jul. 29, 2011

(86) PCT No.: PCT/IB2011/053392
§ 371 (c)(1),
(2), (4) Date: Aug. 5, 2013

(87) PCT Pub. No.: WO2012/014183
PCT Pub. Date: Feb. 2, 2012

(65) Prior Publication Data
US 2013/0317198 A1    Nov. 28, 2013

Related U.S. Application Data

(60) Provisional application No. 61/369,557, filed on Jul. 30, 2010.

(51) Int. Cl.
| *C07K 1/16*  | (2006.01) |
| *C07K 1/18*  | (2006.01) |
| *C07K 1/22*  | (2006.01) |
| *C07K 1/36*  | (2006.01) |
| *C07K 16/00* | (2006.01) |

(52) U.S. Cl.
CPC ............... *C07K 1/165* (2013.01); *C07K 1/18* (2013.01); *C07K 1/22* (2013.01); *C07K 1/36* (2013.01); *C07K 16/00* (2013.01)

(58) Field of Classification Search
None
See application file for complete search history.

(56) References Cited

U.S. PATENT DOCUMENTS

| 2003/0118592 A1 | 6/2003 | Ledbetter et al. |
| 2003/0133939 A1 | 7/2003 | Ledbetter et al. |
| 2004/0241878 A1 | 12/2004 | Thommes et al. |
| 2005/0136049 A1 | 6/2005 | Ledbetter et al. |
| 2007/0060741 A1 | 3/2007 | Kelley et al. |
| 2007/0066806 A1 | 3/2007 | Coffman et al. |
| 2011/0073548 A1* | 3/2011 | Williams et al. ............. 210/739 |

FOREIGN PATENT DOCUMENTS

| WO |        02056910    | 7/2002 |
| WO |        03025156    | 3/2003 |
| WO |     2005017148     | 2/2005 |
| WO |     2005037989     | 4/2005 |
| WO | WO 2005077130 A2 * | 8/2005 |
| WO |     2009045897     | 4/2009 |
| WO |     2009058769     | 5/2009 |

OTHER PUBLICATIONS

Kelley BD, Tobler SA, Brown P, Coffman JL, Godavarti R., Iskra T., Switzer M., Vunnum S., Biotechnol Bioeng., Oct. 15, 2008; 101(3): 553-66).
Graham, et al., J. Gen. Virol., 35:59 (1997).
Urlaub and Chasin, Proc. Natl. Acad. Sci. USA, 77:4216 (1980).
Mather, Biol. Reprod., 23:243-251 (1980).
Shinkawa, et al., J. Biol. Chem., 278:3466-3473, 2003.
Mather, et al., Annals N.Y. Acad Sci., 383:44-68 (1982).

* cited by examiner

*Primary Examiner* — Daniel E Kolker
*Assistant Examiner* — James Rogers

(57) ABSTRACT

The present disclosure provides methods for purifying products from a fluid. In some embodiments, provided purification methods use a combination of purification modes (e.g., protein A and ion exchange) operated in tandem, wherein at least one of the modes utilizes weak partitioning. In some embodiments, provided purification methods operate under robust conditions in which a degree of binding between a product and resin is maintained despite variations in operating parameters.

17 Claims, 17 Drawing Sheets

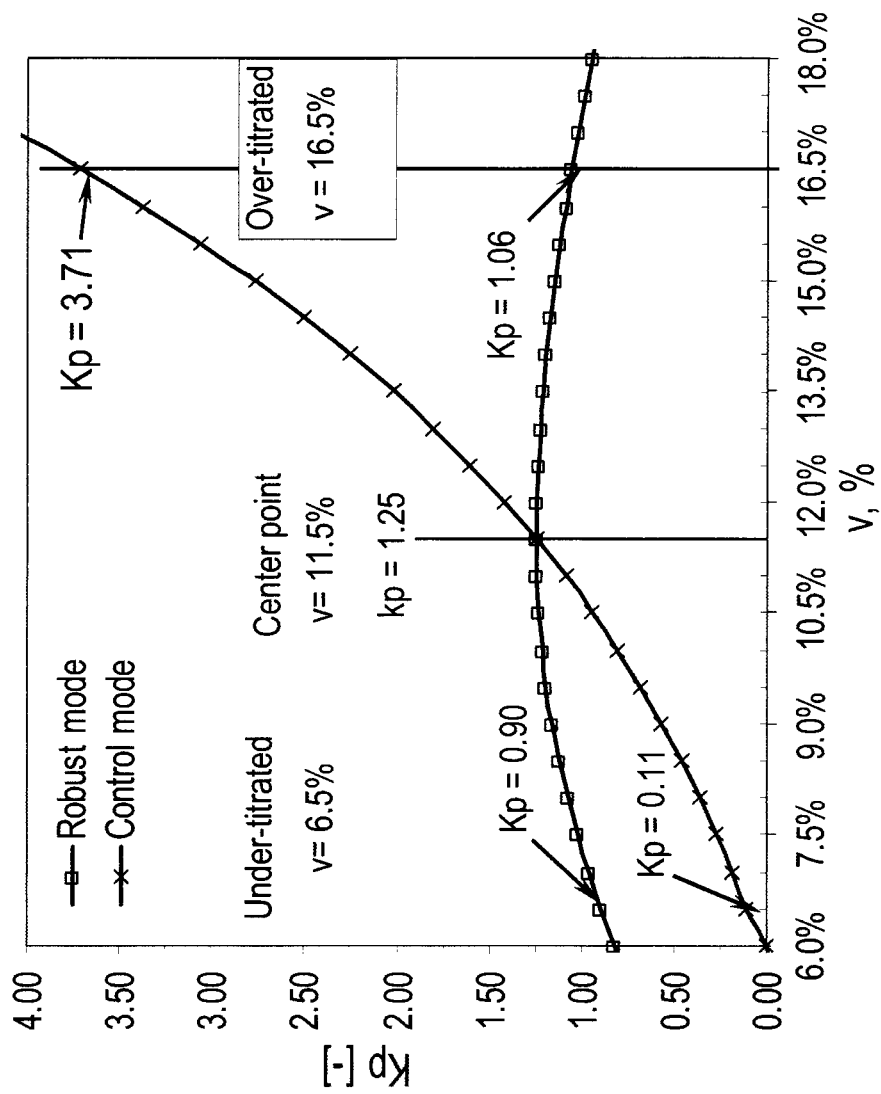

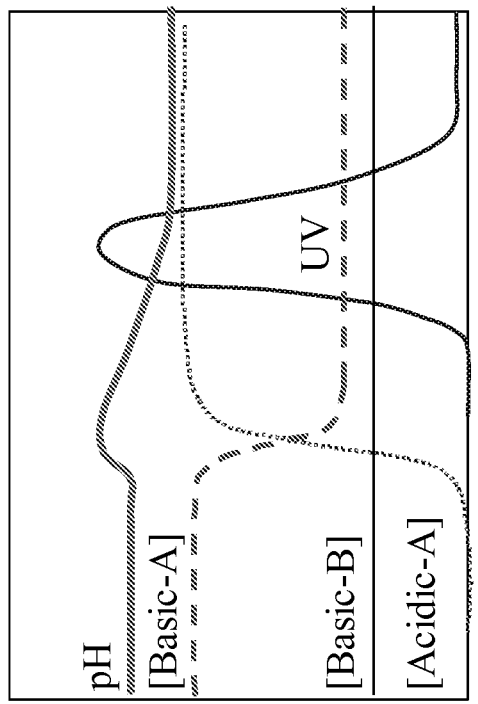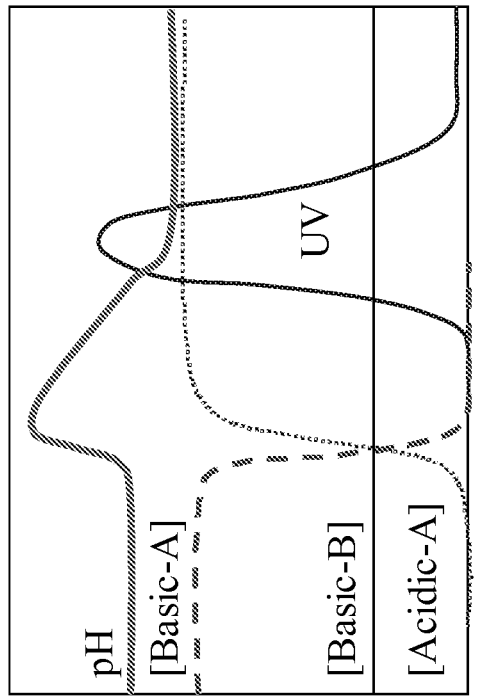

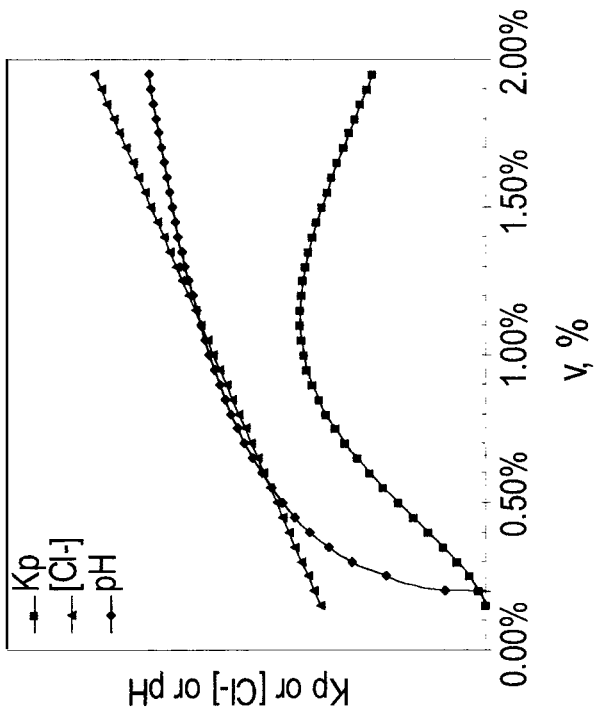
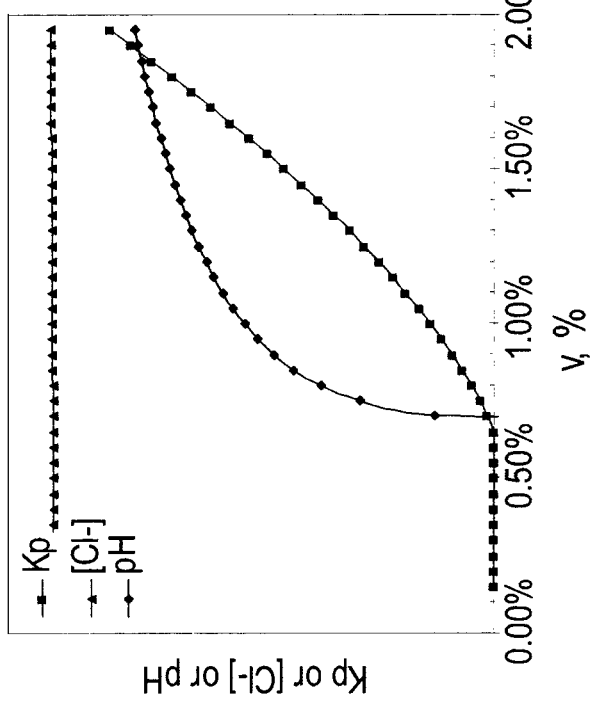
FIG. 13A
FIG. 13B

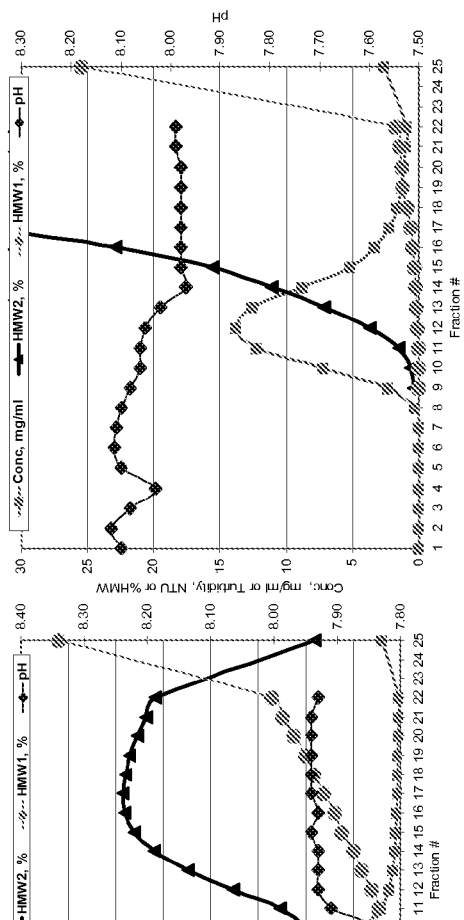
FIG. 15A  FIG. 15B  FIG. 15C
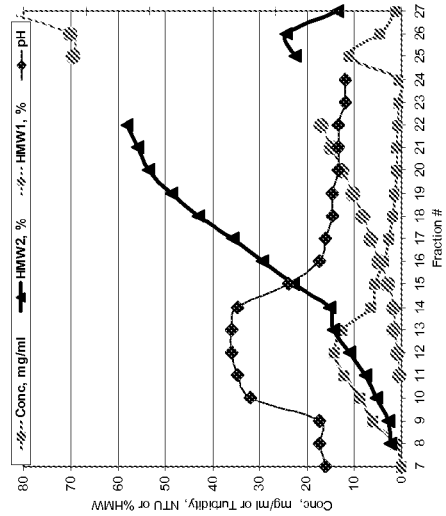

TANDEM PURIFICATION OF PROTEINS

RELATED APPLICATIONS

This application is a national phase application under 35 U.S.C. §371 of PCT International Application No. PCT/IB2011/053392, filed Jul. 29, 2011, which claims the benefit of U.S. Provisional Patent Application No. 61/369,557, filed Jul. 30, 2010, the entire contents of which are hereby incorporated by reference.

BACKGROUND

Proteins must have a certain degree of purity for commercial applications such as therapeutic and diagnostic uses. Recombinant proteins are typically produced in cultured eukaryotic or prokaryotic cells engineered to express a gene encoding the protein. Expressed proteins are separated from impurities such as unrelated host cell proteins, other host cell components (e.g., DNA, cell membranes, etc.) and media components. Purification techniques such as affinity chromatography, ion exchange chromatography, size exclusion chromatography, hydrophobic interaction chromatography, immobilized metal affinity chromatography, and hydroxyapatite chromatography, separate impurities based on differences in size, charge, solubility, hydrophobicity, and/or affinity for a ligand. It is a struggle for companies in the field of pharmaceuticals to develop purification processes that meet stringent regulatory standards in a cost effective way.

SUMMARY

In order to attain the appropriate degree of purity for the commercial use of therapeutic and diagnostic proteins, purification protocols often require use of two or more purification steps. Challenges are presented by more complex purification schemes. For example, product pools processed by one purification mode must be made compatible for processing in a second purification mode. Also, partially processed product pools must be properly stored when downstream purification systems are not immediately available for use. Multiple systems necessitate multiple sampling and validation steps to ensure consistent and proper operation. Systems that integrate multiple purification modes would potentially reduce the complexity of current purification schemes, thereby enhancing the efficiency and reducing the cost of handling manufactured proteins.

The present disclosure provides, inter alia, methods of purifying proteins using systems in which purification units are linked in tandem, and that allow robust operation of purification units. Methods that maintain robustness over variations in operating parameters (e.g., pump speed, volumetric addition of titrants, etc.) require less feedback control and are more cost effective, thereby, in practice, reducing the cost of goods of purified proteins. Integrating purification units eliminates the need to store partially processed product pools between runs. Product may be processed in single shifts, reducing purification time. Integration also reduces sampling, validation, and documentation requirements (e.g., bioburden sampling, batch record documentation, etc.). Variations in parameters such as flow rates, back pressure, and mixing of titrant and eluate between columns may alter product binding and compromise product recovery and quality. Features of the present methods provide a high tolerance to such variations.

Accordingly, in one aspect, the present disclosure provides methods of recovering a purified product (e.g., a protein product; e.g., an antibody) from a fluid. In some embodiments, a method includes: a) exposing a load fluid comprising a protein product to a column comprising a first resin under conditions in which the product binds to the resin; b) recovering fluid comprising the product from the first resin to produce a first eluate; c) titrating the first eluate with a titrant as it passes to the second resin, d) exposing the titrated eluate to a column comprising the second resin under conditions in which the product binds to the second resin, wherein the column comprising the first resin is arranged in tandem with the column comprising the second resin; and e) recovering fluid comprising the product from the second resin to produce a second eluate, thereby recovering a purified protein product from a load fluid.

In some embodiments, a titrant alters one or more conditions of the first eluate such when volumetric ratio of the eluate to the titrant varies by up to 40%, the change in partition coefficient (Kp) of the product for the second resin is less than 10%.

A first eluate can be titrated with a titrant at a variety of volumetric ratios. In some embodiments, a first eluate is titrated with the titrant in a volumetric ratio of between about 95:5 to 80:20. In some embodiments, an eluate is titrated with a fixed volumetric ratio of the titrant.

In some embodiments, flow of fluids through a tandem system of purification units is facilitated by one or more pumps. For example, in some embodiments, a first pump delivers a load fluid to a first resin, a second pump delivers a titrant to the first eluate. Pumps can be operated at a ratio of flow rates that varies by less than 30%, 20%, or 10%. In some embodiments, an eluate and titrant are passed through a mixer prior to exposure to a subsequent purification unit. A tandem operation can optionally include a pH monitor for detecting pH at a given stage of purification (e.g., prior to a purification unit, the operation of which is affected by pH).

In some embodiments, purification methods include passing a fluid through one or more filters (e.g., a 0.2 µm filter). In some embodiments of a tandem purification method, a filter is placed between two columns.

In addition to, or alternative to filters, solids can be removed fluids by precipitation. In some embodiments, solids are precipitated from a fluid using a polymeric flocculant. In some embodiments, solids are precipitated from a fluid using a cation and anion that form a salt having low solubility (e.g., wherein the solubility product constant of a salt having the cation and anion is less than about $10^{-4}$ $M^2$; e.g., using calcium and phosphate).

In some embodiments, a load fluid exposed to a series of purification units includes a cell culture medium. A cell culture medium may be one in which cells have been removed (e.g., by centrifugation). In some embodiments, a cell culture medium may be serum free (e.g., lacking added proteins and/or added animal products).

Methods provided herein can be used to recover various types of products of interest. In many embodiments, a product is a protein such as an antibody (e.g., a monoclonal antibody, antibody fragment, single chain antibody, etc.), Fc fusion protein, or a small modular immunopharmaceutical (SMIP™). Purification of antibodies, Fc fusion proteins, and/or small modular immunopharmaceuticals can include use a resin that selectively binds immunoglobulins, such as protein A (proA).

In various embodiments of methods provided herein, a titrant alters one or more conditions of the first eluate such that product in the titrated eluate binds to the second resin in a weak partitioning mode. For example, conditions of a titrated eluate and a resin can be such that the partition coefficient (Kp) of the product for the resin is 0.1-20 (e.g., 0.2-10, or 0.5-5). In some embodiments, a titrant alters one or more conditions of the first eluate such that the second resin binds to at least 1 mg of product per mL of the resin (e.g., at least 5 mg, 10 mg, 20 mg, 40 mg, 50 mg, or 60 mg of product per mL).

In methods provided herein, pH of a titrated eluate exposed to a second resin can be variable.

Methods provided herein can include use of an ion exchange resin. In some embodiments, the ion exchange resin is an anion exchange resin. In some embodiments, the titrant has a pH which is 0.5 pH units above a pH at which the anion exchange resin binds to product in the titrated eluate in a weak partitioning mode.

In some embodiments, a titrant comprises a salt. A titrant can be used which increases ionic strength of an eluate of a first resin such that a product maintains binding to a second resin (e.g., an ion exchange resin) over a range of titrant volume additions. In some embodiments, a titrant has a salt concentration of at least 50 mM (e.g., at least 100 mM, 150 mM, 200 mM, 250 mM, 500 mM, 750 mM, 1M, or more).

In some embodiments, an ion-exchange resin used in a method provided herein is a cation exchange resin.

Fluids processed by provided methods can be treated with one or more virus reduction treatments such as acid inactivation, detergent inactivation, passage through a virus reduction filter, or a combination thereof. In some embodiments, a virus inactivation treatment used in a method does not include acid inactivation. In some embodiments, a method includes treating a load fluid with a detergent prior to exposing the load fluid to a first resin in a tandem system. In some embodiments in which a virus reduction filter is used, a pump delivers fluid to the filter.

Methods can include viscosity reducing treatments can be used, e.g., heat, addition of salt, alteration of pH, or a combination thereof.

In certain embodiments, a first resin is a protein A resin, a second resin is an ion exchange resin, and a product is recovered from the first resin in a fluid comprising a buffer which has a pKa that is near conditions under which the product elutes from the first resin and a buffer having a pKa near conditions under which the product binds to the second resin in a weak partitioning mode. In some embodiments, a product is recovered from a first resin in a fluid comprising a buffer which has a pKa greater than 5.5 (e.g., Tris).

In another aspect, the present disclosure provides methods of preparing a load fluid for exposure to an ion exchange resin. A method includes, for example: a) providing a load fluid comprising a protein product that binds to the ion exchange resin; and b) adding a titrant to the load fluid, wherein the titrant increases ionic strength of the load fluid such that the product maintains binding to the ion exchange resin over a range of titrant volume additions.

In some embodiments, the load fluid is an eluate of a protein A resin.

In some embodiments, a method includes exposing the titrated eluate to the ion exchange resin under conditions in which the product binds to the resin.

In some embodiments, the ion exchange resin is an anion exchange resin.

Methods can further include exposing a load fluid (e.g., a second eluate) to one or more additional resins and recovering fluid comprising the product from the resin(s). In some embodiments, a load fluid is exposed to a hydroxyapatite resin (e.g., a ceramic hydroxyapatite resin), a hydrophobic interaction resin, a metal affinity resin, an ion exchange resin, or a combination thereof.

In another aspect, the present disclosure provides methods of preparing a load fluid for exposure to an ion exchange resin. A method includes, for example: a) providing a load fluid comprising a protein product that binds to the ion exchange resin; and b) adding a titrant to the load fluid, wherein the titrant has a salt concentration of at least 50 mM (e.g., at least 100 mM, 150 mM, 200 mM, 250 mM, 500 mM, 750 mM, 1M, or more).

In some embodiments, the load fluid is an eluate of a protein A resin.

In some embodiments, a method includes exposing the titrated eluate to the ion exchange resin under conditions in which the product binds to the resin.

In some embodiments, the ion exchange resin is an anion exchange resin.

Methods can further include exposing a load fluid (e.g., eluate of an anion exchange resin) to one or more additional resins and recovering fluid comprising the product from the resin(s). In some embodiments, a load fluid is exposed to a hydroxyapatite resin (e.g., a ceramic hydroxyapatite resin), a hydrophobic interaction resin, a metal affinity resin, an ion exchange resin, or a combination thereof.

In still another aspect, the present disclosure provides methods of recovering a purified protein product from a load fluid. A method includes, for example: a) exposing a load fluid comprising a protein product to a column comprising a first resin under conditions in which the product binds to the resin, wherein the first resin is a protein A resin; b) eluting fluid comprising the product from the first resin to produce a first eluate, wherein the product is eluted from the first resin in an elution fluid comprising a buffer which has a pKa that is near conditions under which the product elutes from the resin and a buffer having a pKa near conditions under which the product binds to the second resin in a weak partitioning mode; c) titrating the first eluate with a titrant as it passes to the second resin; d) exposing the titrated eluate to a column comprising the second resin under conditions in which the product binds to the second resin; and e) recovering fluid comprising the product from the second resin to produce a second eluate, thereby recovering a purified protein product from a load fluid.

In some embodiments, the column comprising the first resin is arranged in tandem with the column comprising the second resin. In some embodiments, the second resin is an ion exchange resin (e.g., an anion exchange resin, or a cation exchange resin).

Methods can further include exposing a load fluid (e.g., a second eluate) to one or more additional resins and recovering fluid comprising the product from the resin(s). In some embodiments, a load fluid is exposed to a hydroxyapatite resin (e.g., a ceramic hydroxyapatite resin), a hydrophobic interaction resin, a metal affinity resin, an ion exchange resin, or a combination thereof.

In another aspect, the disclosure provides methods of recovering a purified protein product from a load fluid. A method includes, for example: a) exposing a load fluid comprising a protein product to a column comprising a first resin under conditions in which the product binds to the resin, wherein the first resin is a protein A resin; b) eluting fluid comprising the product from the first resin to produce a first eluate, wherein the product is eluted from the first resin in an elution fluid comprising a buffer which has a pKa greater than 5.5; c) titrating the first eluate with a titrant as it passes to the second resin; d) exposing the titrated eluate to a column comprising the second resin under conditions in which the product binds to the second resin; and e) recovering fluid comprising the product from the second resin to produce a second eluate, thereby recovering a purified protein product from a load fluid.

In some embodiments, the column comprising the first resin is arranged in tandem with the column comprising the second resin. In some embodiments, the second resin is an ion exchange resin (e.g., an anion exchange resin, or a cation exchange resin).

Methods can further include exposing a load fluid (e.g., a second eluate) to one or more additional resins and recovering fluid comprising the product from the resin(s). In some embodiments, a load fluid is exposed to a hydroxyapatite resin (e.g., a ceramic hydroxyapatite resin), a hydrophobic interaction resin, a metal affinity resin, an ion exchange resin, or a combination thereof.

In still another aspect, the present disclosure provides methods of recovering a purified protein product from a load fluid. A method includes, for example: a) exposing a load fluid comprising a protein product to a protein A column comprising under conditions in which the product binds to the protein A; b) eluting fluid comprising the product from the protein A column to produce a first eluate, wherein the product is eluted from the first resin in an elution fluid comprising a buffer which has a pKa that is near conditions under which the product elutes from the resin and a buffer having a pKa near conditions under which the product binds to the second resin in a weak partitioning mode; and c) titrating the first eluate with a titrant as it elutes from the protein A column, wherein the titrant alters one or more conditions of the first eluate such that product in the titrated eluate binds to an anion exchange resin in a weak partitioning mode, wherein the titrant alters one or more conditions of the first eluate such when volumetric ratio of the eluate to the titrant varies by up to 40%, the change in partition coefficient of the product for the second resin is less than 10%, and wherein the titrant increases ionic strength of the eluate of the first resin such that the product maintains binding to the second resin over a range of titrant volume additions; d) exposing the titrated eluate to a column comprising the anion exchange resin under conditions in which the product binds to the anion exchange resin, wherein the protein A column is arranged in tandem with the column comprising the anion exchange resin; and e) recovering fluid comprising the product from the anion exchange resin to produce a second eluate, thereby recovering a purified protein product from a load fluid.

In some embodiments, a first eluate is titrated with the titrant in a volumetric ratio of between about 95:5 to 80:20.

In some embodiments, flow of fluids through a tandem system of purification units is facilitated by one or more pumps. Pumps can be operated at a ratio of flow rates that varies by less than 30%, 20%, or 10%.

In some embodiments, a load fluid exposed includes a cell culture medium, e.g., a cell culture medium from which cells have been removed (e.g., by centrifugation).

In some embodiments, a product is a protein such as an antibody (e.g., a monoclonal antibody, antibody fragment, single chain antibody, etc.), an Fc fusion protein, or a small modular immunopharmaceutical (SMIP™).

In some embodiments, conditions of a titrated eluate and a resin can be such that the partition coefficient (Kp) of the product for the resin is 0.1-20 (e.g., 0.2-10, or 0.5-5). In some embodiments, a titrant alters one or more conditions of the first eluate such that the second resin binds to at least 1 mg of product per mL of the resin (e.g., at least 5 mg, 10 mg, 20 mg, 40 mg, 50 mg, or 60 mg of product per mL).

In some embodiments, the titrant has a pH which is 0.5 pH units above a pH at which the anion exchange resin binds to product in the titrated eluate in a weak partitioning mode.

In some embodiments, a titrant comprises a salt. In some embodiments, a titrant has a salt concentration of at least 50 mM (e.g., at least 100 mM, 150 mM, 200 mM, 250 mM, 500 mM, 750 mM, 1M, or more). Methods can further include exposing a load fluid (e.g., a second eluate) to one or more additional resins and recovering fluid comprising the product from the resin(s). In some embodiments, a load fluid is exposed to a hydroxyapatite resin (e.g., a ceramic hydroxyapatite resin), a hydrophobic interaction resin, a metal affinity resin, an ion exchange resin, or a combination thereof.

Also provided are systems for practicing provided methods.

Details of certain embodiments of the present disclosure are set forth in the accompanying drawings and the description below. Other features, objects, and advantages of the present disclosure will be apparent from the description and drawing, and from the claims. All cited patents, and patent applications and references are incorporated by reference in their entireties for all purposes.

BRIEF DESCRIPTION OF THE FIGURES

FIG. 4A. Flocculated and pad-filtered load. FIG. 4B. Pad filtered load, no flocculation. Fraction A5 corresponds to a peak apex, with protein concentration of 55 mg/ml.

FIG. 6A. In a Control mode (current state of art) of tandem neutralization, where no salt is added to the neutralization buffer. FIG. 6B. In an (inventive) Robust mode of tandem neutralization, where salt is added to the neutralization buffer.

FIG. 7A. Control mode (current state of art). FIG. 7B. An (inventive) Robust mode, showing the region of overlap.

FIG. 8 is a graph showing simulated Kp=f(v) for the Control (squares) and Robust (crosses) modes of tandem proA-trimethylalaminoethyl (TMAE) purification of a therapeutic MAb. The plot shows three experimentally tested conditions.

FIGS. 12A and 12B are sketches of tandem proA-AEX chromatograms showing concentrations of Basic (high pKa) and Acidic (low pKa) buffer components supplied by pumps A and B post neutralization: FIG. 12A. Current state of art: pH undergoes an upswing due to over-titration. FIG. 12B. Inventive conditions: Basic buffer is present in the elution buffer in a fully protonated state, providing resistance against the pH swing upon neutralization.

FIGS. 13A and 13B are graphs showing examples of pH, [Cl⁻] and Kp as functions of v for batch neutralization. FIG. 13A. In a Control mode (current state of art), where no salt is added to the neutralization buffer. FIG. 13B. In a Robust mode (provided herein), where salt is added to the neutralization buffer.

FIG. 14A. Kp=f(v) plot showing three titration scenarios; FIG. 14B. Relative Kp change function, k. The highlighted area shows the robust operating window.

FIGS. 15A, 15B, and 15C are graphs showing a comparison processes for of purification of a small modular immunopharmaceuticals. FIG. 15A shows results for a control (batch) AEX purification. FIGS. 15B and 15C show results for tandem proA-AEX chromatography at Kp=1.5 without Tris in the protein A elution buffer (FIG. 15B) and with Tris in the elution buffer (FIG. 15C). Offline measurements of pH (diamonds), protein concentration (squares) and HMW species (triangles, circles) are plotted.

FIG. 16A shows results for a control (batch) AEX purification. FIGS. 16B and 16C show results for tandem proA-AEX chromatography at Kp=3.0 without Tris in the protein A elution buffer (FIG. 16B) and with Tris in the elution buffer (FIG. 16C). Offline measurements of pH (diamonds), protein concentration (squares) and HMW species (triangles, circles) are plotted.

DEFINITIONS

Figure 1:
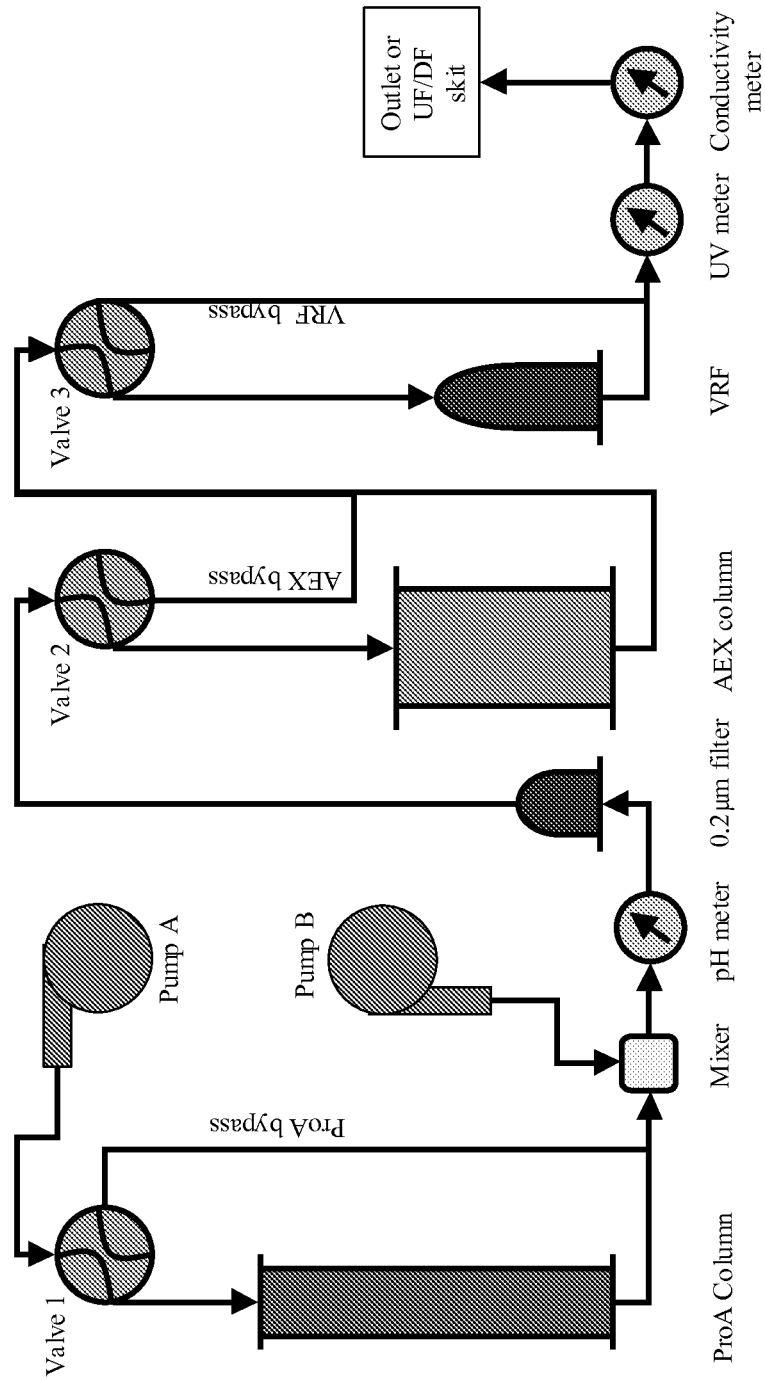
FIG. 1 is a schematic depiction of an exemplary tandem operation of a protein A (ProA) column, anion exchange (AEX) column, and virus reduction filter (VRF).

The term "antibody", as used herein, refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. The term "antibody" also includes antibody fragments such as Fab, F(ab')$_2$, Fv, scFv, Fd, dAb, nanobodies, immunoglobulin new antigen receptors (IgNARS), maxibodies, minibodies, intrabodies, diabodies, triabodies, tetrabodies, and other molecules that retain antigen-binding function. Typically, such fragments would comprise an antigen-binding domain.

In certain embodiments, an antibody is one which comprises a $C_{H2}/C_{H3}$ region and therefore is amenable to purification by protein A chromatography. The term "$C_{H2}/C_{H3}$ region" refers to those amino acid residues in the Fc region of an immunoglobulin molecule which interact with Protein A. In some embodiments, a $C_{H2}/C_{H3}$ region comprises an intact $C_{H2}$ region followed by an intact $C_{H3}$ region, and in other embodiments, comprises a Fc region of an immunoglobulin. Examples of $C_{H2}/C_{H3}$-region-containing proteins include antibodies, immunoadhesions and fusion proteins comprising a protein of interest fused to, or conjugated with, a $C_{H2}/C_{H3}$ region.

A "bound product" (O), as used herein, refers to the amount of product which binds to a resin when in equilibrium with a feedstream.

An "eluate", as used herein, refers to a fluid that has been exposed to a resin. An eluate may be a fluid that includes a load fluid that has been exposed to a resin (e.g., "flow through" fluid); a wash fluid (e.g., a wash buffer) that has been exposed to a resin; an isocratic wash fluid that has been exposed to a resin; an elution fluid that has been exposed to a resin; and combinations thereof. "Eluates" include fluids recovered from resins operated in flow through, weak partitioning, and bind elute chromatographic modes.

An "impurity", as used herein, refers to any molecule other than a protein of interest being purified that is also present in a sample of the protein of interest being purified. Impurities include biological macromolecules such as a DNA, an RNA, proteins, protein variants, such as aggregated proteins, high molecular weight species, low molecular weight species and fragments, and deamidated species; other proteins from host cells that secrete the protein being purified (host cell proteins); molecules that are part of an absorbent used for chromatography that may leach into a sample during prior purification steps, such as Protein A; endotoxins; cell debris; and viruses.

"Isocratic chromatography", as used herein, refers to operation of a chromatographic column with a solvent that does not change strength during the period of interest.

An "essentially isocratic wash", as used herein, refers to a solution which varies only slightly from a load fluid in composition and/or pH.

A "load", as used herein, refers to any material containing a product of interest. A "load fluid" refers to any liquid containing the load. In some embodiments, a "load fluid" is exposed to a purification resin. In some embodiments, a load fluid is a cell culture medium. A cell culture medium may be clarified (e.g., to remove cells or cell debris).

A "partition coefficient" (Kp), as used herein, refers to the equilibrium ratio of the concentration of product absorbed to the resin (O) to the concentration of product in the solution (c), under specified conditions of pH and solution composition. The partition coefficient Kp is also related to the product adsorption isotherms. The partition coefficient Kp corresponds to the slope of the product adsorption isotherm at very low solution concentrations. It is related to the maximum capacity as follows: $Kp=Q/C=Q_{max}/k_d$ where $Q_{max}$ is to maximum capacity of the resin for the product, and $k_d$ is the dissociation constant for 'resin—product' interaction. In some embodiments, a partition coefficient is measured with a batch binding technique. Other techniques, such as isocratic chromatography, can also be used.

A "protein" or "polypeptide", as used herein, refers to any molecule comprising a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. In some embodiments, a protein has a chain comprising more than 5, 10, 20, 50, 100, or 200 amino acids. A protein can include one or more separate amino acid chains. Proteins include naturally produced or recombinant proteins produced in prokaryotic or eukaryotic cells (e.g., primary cells or cell lines).

A "purification unit", as used herein, refers to a physical unit that can be used to perform a mode of purification, e.g., in a tandem purification system. In some embodiments, a purification unit is a vessel (e.g., a column) comprising a resin. In some embodiments, a purification unit is a filter. Purification techniques herein can be practiced in column, membrane, and/or expanded bed adsorption formats, for example.

A "resin", as used herein, refers to any substance that can be used for separation of a product from an impurity. In some embodiments, a resin is a resin that binds to immunoglobulins, e.g., a protein A resin). In some embodiments, a resin is an ion exchange resin (e.g., an anion exchange resin, or a cation exchange resin).

A "small modular immunopharmaceutical" or "SMIP™", refers to a binding domain—immunoglobulin fusion protein that has a binding domain for a cognate structure such as an antigen, an immunoglobulin hinge region (which may or may not include amino acid substitutions relative to a wild type sequence), and immunoglobulin $C_{H2}$ and $C_{H3}$ domains. Small modular immunopharmaceuticals are described, e.g., in US Pat. Pubs. 2003/133939, 2003/0118592, 2005/0136049, and WO 02/056910, WO 2005/037989, and WO 2005/017148.

A "weak partitioning mode", as used herein, refers to a product preparation separation technique in which at least one product contained in the preparation, and at least one contaminant or impurity, both bind to a chromatographic resin. The binding of product in weak partitioning mode is at least 1 mg of product per mL of chromatographic resin or medium. Generally, the product partition coefficient for weak partitioning mode is at least 0.1. A "weak partitioning mode" is an isocratic operation. Separation using a weak partitioning mode is described in U.S. Pub. No. 2007/0060741, the entire contents of which are hereby incorporated by reference.

DETAILED DESCRIPTION OF CERTAIN EMBODIMENTS

Tandem Methods and Systems

The present disclosure provides methods and systems in which two or more purification units are operated in tandem, i.e., such that a load fluid can be exposed to multiple purification units in series. In some embodiments, a purification system includes a first resin and a second resin, wherein the second resin is one which can operate in a weak partitioning mode (e.g., an ion exchange resin). An exemplary tandem system is shown in FIG. 1. In this exemplary system, a Protein A column, an AEX column, and a VRF filter are linked.

Valves in a tandem system can be placed so as to allow any combination of purification units to operate in line. For example, valves placed downstream of a first resin can remain closed while a load fluid is applied to the first resin and opened after the first resin is washed. A fluid passing through a purification unit may be directed to subsequent purification units (e.g., to wash, equilibrate, load, or elute from a subsequent purification unit) or discarded, as desired. Purification units may be washed and/or regenerated separately (e.g., with a fluid directed only through the individual unit, or a fluid from an upstream unit), as required and/or as desired by the practitioner. In some embodiments, a system provided herein is a simulated moving bed system.

Operation of multiple purification units in series may produce undesirable levels of pressure or changes in pressure within the system. Pressure buildup can be alleviated by various approaches. Pumps can be placed to promote flow before, between, and/or after one or more purification units. Fluids may be treated to reduce viscosity and/or remove impurities that may precipitate, interfere with flow, and cause an increase in pressure in the system. In some embodiments, a fluid in the system is heated to reduce viscosity. In some embodiments, an eluate of the first purification unit is heated to reduce viscosity.

To remove impurities that may precipitate during operation of a tandem system, a load fluid or downstream fluid can be treated to separate the substances from the fluid. In some embodiments, a polymeric flocculant is used. Examples of polymeric flocculants include protamine sulfate, chitosan, DEAE dextran, acrylamide-based polymers, polyethyleneimine, and polyethylene amine. In some embodiments, a combination of a cation and anion that form an insoluble salt is used to remove impurities from a fluid, e.g., a cation and anion that form a salt having a solubility product constant of less than $1\times10^{-4}$ (e.g., $CaPO_4$). Methods of removing impurities are described, e.g., in U.S. Pub. No. 2007/0066806, the entire contents of which are hereby incorporated by reference. Removal of solids can also be achieved by filtration. Any one or combination of methods for removal of precipitating impurities can be used. In some embodiments, a load fluid (e.g., culture medium) is treated to remove impurities that may precipitate, prior to exposure to a first resin.

Many implementations of protein purification methods use virus inactivation or removal steps. One method for inactivating viruses is to lower pH of a fluid. In some embodiments, e.g., embodiments in which low pH is not compatible with a neighboring purification step, viruses are removed by passing a fluid through a virus reduction filter and/or by detergent inactivation. Any of a variety of detergents can be used for virus inactivation, e.g., Tween or Triton X-100. In some embodiments, a load fluid (e.g., culture medium) is treated to remove or inactivate viruses prior to exposure to a first resin.

Weak Partitioning

In various embodiments of methods provided herein, one or more purification steps uses chromatography in a weak partitioning mode. In weak partitioning mode, a product-containing fluid is passed through a resin, with both the product and impurities binding to the resin. However, impurities bind more tightly than the product. As loading continues, unbound product passes through the resin and is recovered in the column effluent. In some embodiments, a resin is washed (e.g., with an isocratic wash) to recover additional weakly bound product.

A weak partitioning mode is defined by conditions in which a resin binds at least 1 mg of product per mL of resin (e.g., at least 5, 10, 20, 30, 40, 50, or 60 mg per mL). A weak partitioning mode is also defined by a partition coefficient (Kp) of at least 0.1. In some embodiments, operation in a weak partitioning mode comprises operating under conditions defined by a Kp in the range of about 0.2-20 (e.g., 0.2-10, or 0.5-5). In contrast to weak partitioning, a bind-elute mode is typically defined by a Kp over 20 and employs a change in buffer composition after load to cause elution of product. A flow through mode is typically defined by a Kp<0.1 and employs an isocratic wash to recover product.

Kp is calculated from batch-binding experiments as the ratio of adsorbed protein concentration to free protein concentrations at equilibrium. Kp is a function of pH and concentration of ions in equilibration, loading and wash buffers. In some embodiments, for a weak partitioning mode, an AEX step is operated between Kp=1 and Kp=3 (see U.S. Pub. No. 2007/0060741 and Kelley B D, Tobler S A, Brown P, Coffman J L, Godavarti R, Iskra T, Switzer M, Vunnum S. *Biotechnol Bioeng.* 2008 Oct. 15; 101(3): 553-66).

Appropriate operating conditions for weak partitioning depend on the choice of resin selected for purification of the product. Conditions can include pH levels and ionic strengths, salt concentrations, and/or excipient levels.

In some embodiments, conditions for weak partitioning are identified by screening. Screening can include batch binding studies or column binding studies. Column binding studies could include gradient elution studies or isocratic elution studies. For example, one skilled in the art can determine which buffer or salt is appropriate for the particular protein being purified and for the operating conditions that are being identified. An optimal concentration of the selected buffer or salt can then be determined by, for example, running a gradient of the selected buffer or salt through a column to which a load fluid comprising the product to be purified and the impurities has been applied. Fractions of the effluent of the column can be collected and analyzed to determine the concentration of buffer or salt at which product binding is at least 1 mg of product per mL of resin or alternatively, at which the partition coefficient for the product is at least 0.1. In some embodiments, the partition coefficient is measured between 1 and 10 mg/mL load challenge with a phase ratio (volume of liquid to volume of resin) of three to six in a batch binding experiment.

Once operating conditions are determined, conditions of the fluid to be applied to a resin in weak partitioning conditions (e.g., an eluate of a prior resin such as protein A) can be adjusted accordingly as described herein. After the fluid is passed through the resin, the resin is optionally washed with a volume of essentially isocratic wash. Purified product can be obtained from any essentially isocratic wash and pooled with the purified product from the column effluent during the load cycle. After the optional wash step, the resin can optionally be stripped and regenerated, e.g., to minimize the buildup of impurities on the surface of the solid phase and/or to sterilize the resin to avoid contamination of the product with microorganisms.

High load concentrations and load volumes are possible with weak partitioning mode. In one embodiment, the concentration of product in the load fluid is at least 1 mg of product per mL of load fluid, in another embodiment, the concentration of product in the load fluid is at least 5 mg of product per mL of load fluid, in another embodiment, at least 50 mg of product per mL of load fluid, and in another embodiment, at least 100 mg of product per mL of load fluid. Purified product can be recovered from up to 50 CVs of load fluid passed through the resin.

In order to obtain accurate formulation in traditional batch chromatography modes, titration of an eluate of a first resin (e.g., a proA resin) may require use of pumps controlled by pH feedback or by pumps delivering programmed ratios of buffers. Methods provided herein add robustness to purification procedures and can eliminate the need for more complex control mechanisms.

In certain embodiments of tandem purification methods provided herein, product is recovered from a first resin in a fluid comprising a buffer. In some embodiments, a pH swing occurs as earlier fractions of an eluate of the first resin are mixed with a titrant. It has been discovered that conditions can be such that, although titrated eluate exhibits a pH swing, buffer in later fractions of the eluate mitigates negative effects of a pH swing on performance of the second resin.

For example, it was found that the pH at the end of a proA elution determines product quality and recovery of the tandem pool, as long as the pH consistently decreases over the course of the elution. Conversely, higher than optimal pH in the beginning of a proA elution would have minimal effect on product quality and recovery. Accordingly, in some embodiments of the present disclosure, methods are provided that include operating a tandem proA-AEX process despite the variable pH. In some embodiments, pump rates in such methods need not vary.

As noted above, a partition coefficient, Kp, is related to pH and solution composition (e.g., ionic strength and buffer composition). It has been discovered that adding salt to a titrant that is used to prepare a fluid for exposure to an ion exchange resin increases robustness of purification by maintaining a steady degree of binding strength over a range of titration ratios. This principle is applicable to tandem and non-tandem methods.

In further embodiments, a tandem purification (e.g., proA-AEX) can be designed in a range of neutralization ratios (v) of eluate to titrant that results in a change in Kp (k) to be less than a certain amount. A robust operating window independent of Kp and v can be described as a function k as follows:

$k = ABS[Kp(v+\Delta v) - Kp(v-\Delta v)]/Kp(v)$, %, which measures an absolute % change in Kp within a given operating range ($v \pm \Delta v$).

For example, in some embodiments, tandem proA-AEX is conducted in a range of neutralization ratios (v) and a combination of parameters that results in the relative change in Kp (k) below 100% when v is varied from 50% to 150% of the target. In some embodiments, tandem proA-AEX is conducted at conditions where k<50%, in the range of 75% to 125% of the target v. In some embodiments, conditions result in k<20%, in the range of 90% to 110% of the target v.

Another aspect for improving purification processes provided herein relates to conditions under which proteins are eluted from proA. It has been discovered that addition of a buffer having a high pKa (e.g., 5.5 or more) to an acidic proA elution buffer provides resistance to variations in pH during subsequent neutralization with a titrant, e.g., in preparation for application to an anion exchange resin. Buffers having a pKa of 5.5 or more are listed in Table A. Any of these may be used in a protein A elution buffer.

TABLE A

Table A. Base pKa Values

| Free Acid or Base | MW | pKa at 25° C. |
|---|---|---|
| Benzenehexacarboxylic (mellitic) | 342.17 | 5.50 ($pK_{a5}$) |
| 2,2-Dimethylglutaric | 160.17 | 5.51 ($pK_{a2}$) |
| Itaconic | 130.1 | 5.55 ($pK_{a2}$) |
| Cyclopentanetetra-1,2,3,4-carboxylic | 246.17 | 5.57 ($pK_{a3}$) |
| Succinic | 118.09 | 5.57 ($pK_{a2}$) |
| Benzene-1,2,4,5-tetracarboxylic (pyromellitic) | 254.15 | 5.61 ($pK_{a4}$) |

TABLE A-continued

Table A. Base pKa Values

| Free Acid or Base | MW | pKa at 25° C. |
|---|---|---|
| Benzene-1,2,3-tricarboxylic (hemimellitic) | 246.18 | 5.87 ($pK_{a3}$) |
| Dimethylmalonic | 132.12 | 5.98 ($pK_{a2}$) |
| Histidine | 156.16 | 6.00 ($pK_{a2}$) |
| Hydroxylamine | 34.0 | 6.03 |
| Carbonic ($H_2CO_3 + CO_2$) | 62($CO_2$) | 6.10 ($pK_{a1}$) |
| Malonic | 104.06 | 6.10 ($pK_{a2}$) |
| 2-(N-Morpholino)-ethane sulfonic acid "MES" | 195.2 | 6.15 ($pK_{a2}$) |
| Glycerophosphoric | 172.08 | 6.19 ($pK_{a2}$) |
| Propane-1,2,3-tricarboxylic (tricarballylic) | 176.12 | 6.20 ($pK_{a3}$) |
| Benzenepentacarboxylic | 298.16 | 6.25 ($pK_{a5}$) |
| Maleic | 116.07 | 6.26 ($pK_{a2}$) |
| 2,2-Dimethylsuccinic | 146.14 | 6.29 ($pK_{a2}$) |
| EDTA | 292.24 | 6.30 ($pK_{a3}$) |
| 3,3-Dimethylglutaric | 160.17 | 6.31 ($pK_{a2}$) |
| Bis(2-hydroxyethyl)imino-tris(hydroxymethyl) methane "BIS-TRIS" | 209.24 | 6.46 |
| Benzenehexacarboxylic (mellitic) | 342.17 | 6.59 ($pK_{a6}$) |
| N-(2-Acetamido)imino-diacetic acid "ADA" | 190.17 | 6.60 ($pK_{a3}$) |
| Butane-1,2,3,4-tetracarboxylic | 234.12 | 6.63 ($pK_{a4}$) |
| Pyrophosphoric | 177.98 | 6.68 ($pK_{a3}$) |
| 1,1-Cyclopentanediacetic (3,3 tetramethylene glutaric acid) | 186.21 | 6.70 ($pK_{a2}$) |
| 1,4-Piperazinebis-(ethanesulfonic acid) "PIPES" | 302.37 | 6.8 ($pK_{a4}$) |
| N-(2-Acetamido)-2-aminoethanesulfonic acid "ACES" | 182.20 | 6.9 ($pK_{a2}$) |
| 1,1-Cyclohexanediacetic | 200.18 | 6.94 ($pK_{a2}$) |
| 3,6-Endomethylene-1,2,3,6-tetrahydrophthalicacid "EMTA" | 183.62 | 7.00 (pK2) |
| Imidazole | 68.08 | 7.00 |
| 2-(Aminoethyl)trimethylammonium chloride "CHOLAMINE" | 156.69 | 7.10 |
| N,N-Bis(2-hydroxyethyl)-2-aminoethanesulfonic acid "BES" | 213.25 | 7.15 ($pK_{a2}$) |
| 2-Methylpropane-1,2,3-triscarboxylic | 190.15 | 7.20 ($pK_{a3}$) |
| 2-(N-Morpholino)propane-sulfonic acid "MOPS" | 209.27 | 7.20 ($pK_{a2}$) |
| Phosphoric | 98.0 | 7.21 ($pK_{a2}$) |
| N-Tris(hydroxymethyl)methyl-2-aminoethane sulfonic acid "TES" | 229.28 | 7.50 ($pK_{a2}$) |
| N-2-Hydroxyethylpiperazine-N'-2-ethanesulfonic acid "HEPES" | 238.31 | 7.55 ($pK_{a2}$) |
| 2-Hydroxyethylimino-tris(hydroxymethyl) methane "MONO-TRIS" | 165.18 | 7.83 |
| Brucine tetrahydrate | 466.53 | 7.95 ($pK_{a2}$) |
| 4-(2-Hydroxyethyl)-1-piperazinepropane sulfonic acid "EPPS" | 252.23 | 8.00 |
| Tris(hydroxymethyl)aminomethane"TRIS" | 121.14 | 8.10 |
| N-Tris(hydroxymethyl)methylglycine "TRICINE" | 180.18 | 8.15 |
| Glycinamide | 74.04 | 8.20 |
| N,N-Bis(2-hydroxyethyl)glycine"BICINE" | 163.18 | 8.35 |
| N-Tris(hydroxymethyl)methyl-2-aminopropane sulfonic acid "TAPS" | 243.3 | 8.40 ($pK_{a2}$) |
| N-Glycyl-glycine | 132.12 | 8.40 |
| Histidine | 155.16 | 9.17 ($pK_{a3}$) |
| Boric | 43.82 | 9.24 |
| Pyrophosphoric | 177.98 | 9.39 ($pK_{a4}$) |
| Ethanolamine | 61.08 | 9.44 |
| Glycine | 75.07 | 9.60 ($pK_{a2}$) |

Resins

Various combinations of resins can be used in methods (e.g., tandem purification methods) provided herein, including bind-elute resins, anion exchange resins, size exclusion resins, hydrophobic interaction resins, immobilized metal affinity resins, and hydroxyapatite resins.

Anionic exchange resins that can be used include resins having substituents such as diethylaminoethyl (DEAE), trimethyaminoethyl (TMAE), quaternary aminoethyl (QAE) and quaternary amine (O) groups.

Cationic exchange resins that can be used include resins having substituents such as carboxymethyl (CM), sulfoethyl (SE), sulfopropyl (SP), phosphate (P) and sulfonate (S).

In some embodiments, a cellulosic ion exchange resin (e.g., DE23, DE32, DE52, CM-23, CM-32 or CM-52, available from Whatman Ltd. Maidstone, Kent, U.K) is used. Sephadex-based and cross-linked ion exchangers used for purification include, for example, DEAE-, QAE-, CM-, and SP-Sephadex, and DEAE-, Q-, CM- and S-Sepharose, and Sepharose (Amersham Biosciences, Piscataway, N.J.). DEAE and CM derivatized ethylene glycol-methacrylate copolymer such as TOYOPEARL™ DEAE-650S or M and TOYOPEARL™ CM-650S or M are available from Toso Haas Co., Philadelphia, Pa.

Commercially available protein A chromatography columns include, for example, PROSEP-A™ (Millipore, U.K.), Protein A Sepharose FAST FLOW™ (GE Healthcare, Piscataway, N.J.), TOYOPEARL™ 650M Protein A (TosoHass Co., Philadelphia, Pa.), and MabSelect™ columns (GE Healthcare, Piscataway, N.J.).

In some embodiments, a hydrophobic interaction chromatography (HIC) resin is used for purification. HIC separates molecules based on hydrophobicity. Generally, sample molecules in a high salt buffer are loaded onto the HIC resin. Salt in the buffer interacts with water molecules to reduce the solution of the molecules in solution, thereby exposing hydrophobic regions in the sample molecules which are consequently absorbed by the HIC medium. The more hydrophobic the molecule, the less salt needed to promote binding. Binding interactions between the product molecules and a HIC medium thus depend on conditions such as pH, ionic strength, and salt concentrations of the medium. Commercially available HIC resins that can be used include resins comprising a base matrix (e.g., cross-linked agarose or synthetic copolymer material) to which hydrophobic ligands (e.g., alkyl or aryl groups) are coupled. Examples include PhenylSEPHAROSE™, 6 FAST FLO™ (Pharmacia LKB Biotechnology, AB, Sweden); Phenyl SEPHAROSE™ High Performance (Pharmacia LKB Biotechnology, AB, Sweden); Octyl SEPHAROSE™ High Performance (Pharmacia LKB Biotechnology, AB, Sweden); Fractogel™ EMD Propyl or FRACTOGEL™ EMD Phenyl (E. Merck, Germany); MACRO-PREP™ Methyl or MACRO-PREP™ t-Butyl Supports (Bio-Rad, CA); WP HI-Propyl $(C_3)$™ (J. T. Baker, N.J.); and TOYOPEARL™ ether, phenyl or butyl (TosoHaas, Pa.). HIC can be performed in a weak partitioning mode.

In some embodiments hydroxyapatite chromatography is used for purification. Hydroxyapatite chromatography utilizes an insoluble hydroxylated calcium phosphate of the formula $[Ca_{10}(PO_4)_6(OH)_2]$, as both the matrix and the ligand. Functional groups consist of pairs of positively charged calcium ions (C-sites) and clusters of negatively charged phosphate groups (P-sites). Binding interactions between a product and a hydroxyapatite medium depend on conditions such as the pH, ionic strength, and excipient concentrations, such as phosphate concentrations, calcium concentrations, arginine concentrations, glycine concentrations, and HEPES concentrations of the medium. Various hydroxyapatite chromatographic resins are available commercially. Hydroxyapatite chromatography can be performed in a weak partitioning mode.

In some embodiments, an immobilized metal affinity chromatography (IMAC) resin is used for purification. IMAC is based on the interaction between chelated transition metal ions immobilized on a resin and imidazole side chains of histidine residues on a tagged product of interest.

Separation of molecules occurs as a result of competition between the tagged product of interest and counterligands for metal groups on the IMAC resin. Binding interactions between a product and metal-charged IMAC medium depend on conditions such as counterligand levels, such as imidazole concentrations, and ionic strength of the medium. Various IMAC resins are available commercially. IMAC can be performed in a weak partitioning mode.

Purification using any of the above resins can occur under conditions known to those of skill in the art and in combination with inventive methods provided herein.

For example, a proA resin can be operated under a variety of conditions. In some embodiments, a proA column is flushed and equilibrated with one or more solutions prior to contact with a load fluid. Such solutions can include, for example, a buffer (e.g., Tris, MES, HEPES, histidine, or phosphate, e.g., between 1-500 mM, 25-100 mM, or 50 mM), and/or salt (e.g., NaCl, NaPO$_4$, sodium acetate, or CaCl$_2$, e.g., between 0-2M, or 5-250 mM). The pH of an equilibration solution is generally between 3.5-10 (e.g., between pH 6.0-8.0).

After contacting a proA resin with a load fluid, bound resin can be washed. Wash solutions can include a buffer (e.g., Tris, MES, HEPES, phosphate, or histidine, e.g., between 1 and 500 mM), and/or salt (e.g., NaCl, CaCl$_2$, NaPO$_4$, or sodium acetate, e.g., between 0 and 2 M), and/or an additive (e.g. guanidine, urea, sucrose, arginine, or an arginine derivative), and/or a solvent (e.g., ethanol, acetonitrile, or polyethylene glycol). Wash solutions generally have a pH between 3.5 and 10 (e.g., a pH between 4.5-8.0). In some embodiments, a resin is washed with the same solution as used to equilibrate the resin.

Polypeptides can be eluted from a proA resin using a step or gradient change in pH, salt type, salt concentration, solvent type, solvent concentration, displacer type, displacer concentration, or a combination thereof. In general, to elute a product from a proA resin, the resin is contacted with an elution buffer. In some embodiments, an elution buffer contains a salt (e.g., NaCl or CaCl$_2$, e.g., e.g., 1-100 mM). In some embodiments, an elution buffer may contain glycine, acetic acid, or citric acid (e.g., 20 mM-250 mM). An elution buffer may also contain a buffer (e.g., HEPES, e.g., 10-100 mM). An elution buffer may also contain acetic acid (e.g., 20 mM to about 50 mM), an additive (e.g. guanidine, urea, or sucrose), and/or a solvent (e.g., ethanol, acetonitrile, polyethylene glycol, e.g., 1-10% solvent, e.g., 5% solvent). The pH of the elution buffer may range from about 2.0 to about 4.0. In some embodiments, pH can be changed (e.g., gradually) to produce a gradient elution (e.g., a gradient elution from pH 5.0 to pH 3.0). In one embodiment, the pH of the elution buffer is about 3.0. An eluate can be neutralized, e.g., by adjusting pH to 6.0-8.0 (in cases in which low pH is used for elution), by adding a titrant as described herein, after recovery from the resin.

Products for Purification

Methods and systems provided herein can be used for purification (e.g., commercial-scale purification) of various products of interest, including naturally occurring proteins, fusion proteins, Fc-containing proteins, immunoconjugates, cytokines, growth factors, G-protein coupled receptors, interleukins, hormones, and enzymes. In some embodiments, a protein undergoing purification may comprise one or more constant antibody immunoglobulin domain(s). In some embodiments, the protein may also comprise a single or multiple variable antibody immunoglobulin domain(s). An Fc-containing protein may comprise an antibody. Proteins can be derived from various sources, including cultured recombinant prokaryotic or eukaryotic host cell lines.

Proteins (e.g., antibodies) for purification according to methods provided herein can be from a number of sources including, but not limited to, serum of immunized animals, ascites fluid, hybridoma or myeloma supernatants, conditioned media derived from culturing a recombinant cell line that expresses the protein molecule and from cell extracts of protein-producing cells. In some embodiments, proteins from conditioned cell culture media of a variety of protein producing recombinant cell lines are purified. In some embodiments, proteins are from commercially available preparations. In some embodiments, an antibody is to be purified.

In some embodiments, a protein for purification according to a method described herein is produced by expression in a recombinant cell. A wide variety of cells can be used to produce a recombinant protein. Any cell that can be transformed with recombinant DNA to express a protein of interest (e.g., a monoclonal antibody), can be used in the methods of the present disclosure. Cells can be from a variety of species, e.g., eukaryotic species, including plant, yeast, nematode, worm, insect, amphibian, or mammal, for example, human, primate, ovine, bovine, porcine, equine, feline, canine, or rodent source. In particular embodiments, the cells are from human or rodent. In particular embodiments, the cells are from hamster (e.g., Chinese hamster ovary cells). Examples of mammalian cells that may be used include BALB/c mouse myeloma line (NSO/I, ECACC No: 85110503); SP2/0; Balb/c 3T3; human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, Proc. Natl. Acad. Sci. USA, 77:4216 (1980); GS-CHO, CHO-K1, CHO-K1SV, CHO-DG44, CHO-DUKX, CHO-DUXB11, CHO-S); mouse sertoli cells (TM4, Mather, Biol. Reprod., 23:243-251 (1980)); rat hybridoma YB2/0 (Shinkawa et al., J. Biol. Chem. 278:3466-3473, 2003); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). A number of suitable cell lines can be obtained from depositories such as the America Type Culture Collection (ATCC), Manassas, Va. Examples of plant cells that may be used include *Lemmna minor* (duckweed), *Arabidopsis thalania*, and *Physcomitrella patens* (moss) cells. Examples of insect cells that may be used include *Spodoptera frugiperda* (Sf9 and Sf21), *Trichoplusia ni* (Tni and BTI-Tn 5B1-4), and *Mamestra brassicae* (Mb) cells. Useful fungal cells include *Pichia pastoris* and *Saccharomyces cerevisiae* cells.

EXEMPLIFICATION

Example 1

Tandem Operation of a Protein A Step, an Anion Exchange (AEX) Chromatographic Step and a Virus Reduction Filter (VRF)

A tandem operation (FIG. 1) of a protein A column, an AEX column (run in weak partitioning mode) and a virus reduction filter (VRF) was implemented at lab scale for purification of MAbs and small modular immunopharmaceuticals. Pumps A and B operate at a constant ratio of flow rates. A mixer ensures a thorough mixing of the ProA effluent delivered by Pump A with 5-20% v/v of titrant delivered by Pump B. Valves 1-3 enable any combination of unit operations to be in-line during the process. For example, during the proA load and wash steps, only the proA column is in-line and pump B is idle. After one proA column volume (CV) of the final high pH/low salt proA wash, valves 2 and 3 open and pump B starts adding a neutralization buffer (titrant) to the proA effluent, which is used to equilibrate the AEX and VRF. All three unit operations remain in-line during the low-pH elution and a part of post-elution proA wash, as the proA effluent is being neutralized and used as a TMAE wash. Alternatively, post-elution wash of the proA column may be directed to waste, and TMAE may be washed with a dedicated buffer. The proA and the AEX columns are regenerated separately. However, the ethanol-containing storage buffer may be applied to both columns in tandem.

Figure 2:
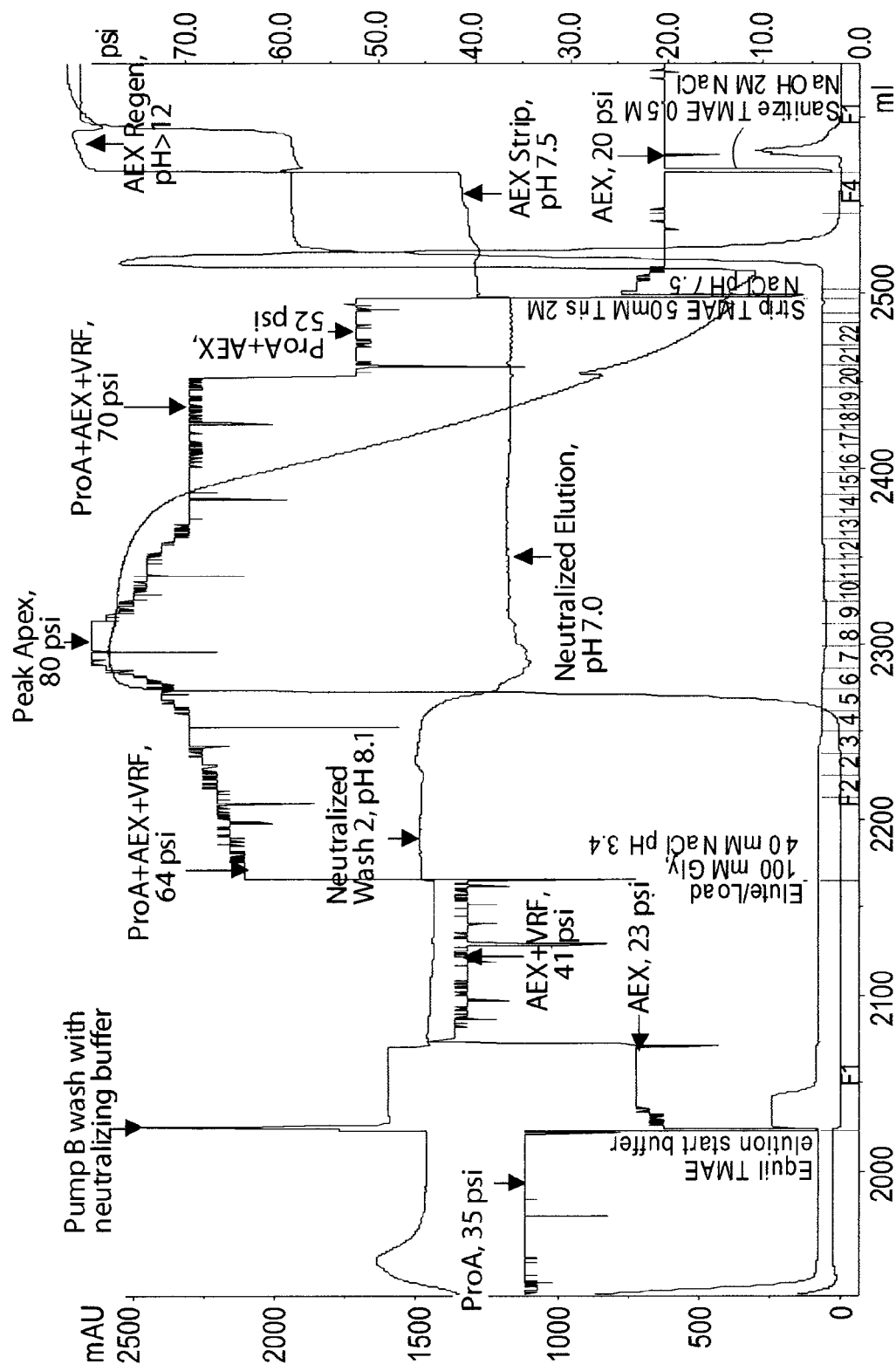
FIG. 2 shows a part of an in-process tandem proA-AEX-VRF chromatogram obtained on an AKTA FPLC system, showing the elution peak and the AEX strip region. UV signal at 280 nm (mAU); total system pressure (psi); pH of neutralized proA effluent; and conductivity of AEX effluent are shown. The pH and pressure readings at each stage of the process were obtained with in-line sensors and may not be accurate.
Figure 3:
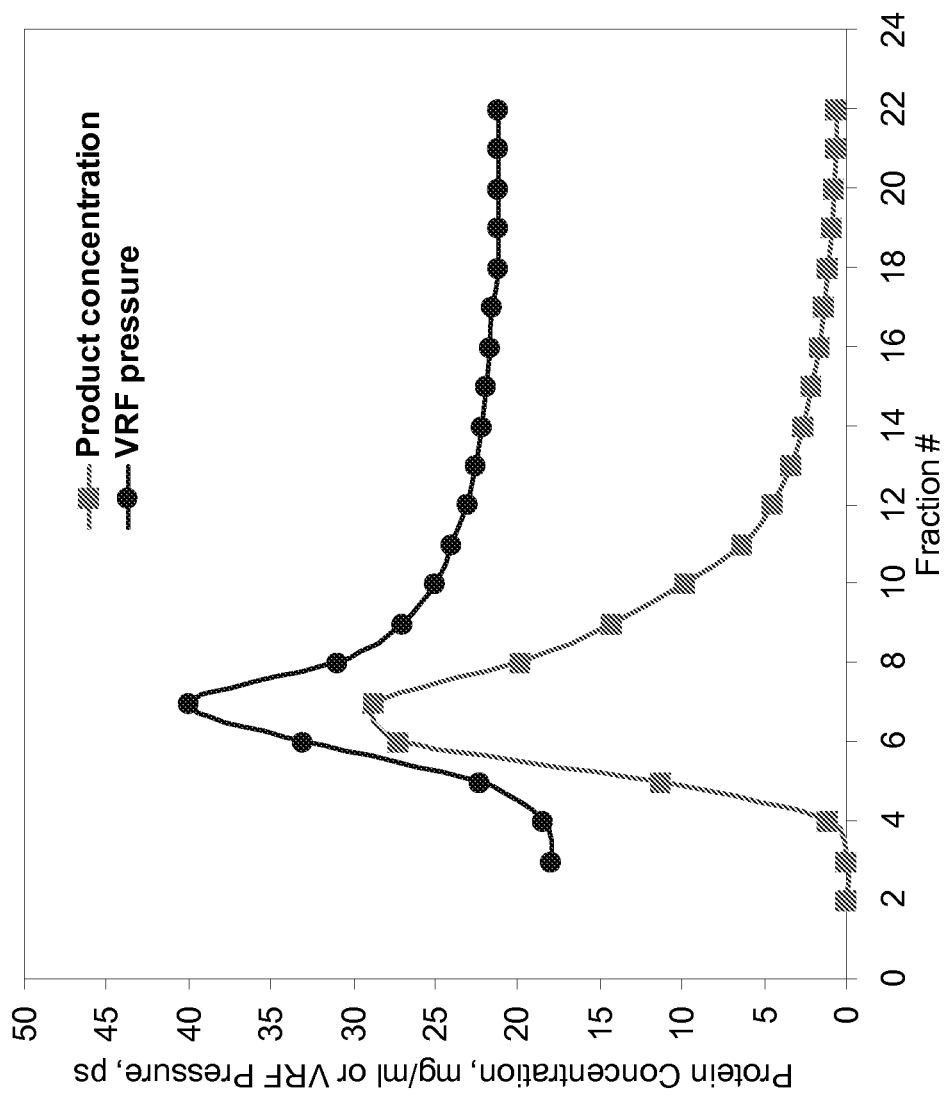
FIG. 3 shows a tandem proA-AEX-VRF chromatogram obtained from an off-line analysis of peak fractions (volume of each fraction=½ of AEX CV). Squares—protein concentration. Circles—pressure across the VRF device.

An example of a tandem proA-AEX-VRF chromatogram, depicting UV, pH and pressure traces during the elution, is shown in FIG. 2. Abrupt changes in pressure were due to switching of the system components on and off. The gradual rise in pressure during the elution correlated with the peak apex passing through the VRF membrane, as shown in FIG. 3. After the elution, the pressure across the VRF returned to almost the pre-elution level, suggesting that the pressure rise had been due to viscosity of the product peak and not to plugging of the membrane.

A tandem process with three unit operations was executed successfully for a number of monoclonal antibodies (MAbs) and small modular immunopharmaceuticals (SMIPs™), demonstrating the feasibility of in-line neutralization. Surprisingly, the system did not experience unacceptably high back pressures due to proA peak precipitation. No pressure increase was observed with reuse, pointing to the absence of fouling.

Example 2

A Tandem proA-AEX Process with a Flocculated proA Load

Precipitation of product, HMW and other impurities often occurs during proA peak elution and neutralization. This process is difficult to control. Solids should be removed from the process stream, as their presence causes fouling of the AEX resin. In some embodiments, removal is accomplished by filtration through a 0.2 µm filter.

Nucleation and growth of solid particles is a kinetically controlled process that sometimes takes hours to proceed to completion. The duration of nucleation does not affect a regular batch chromatography, since there is a significant time lag between proA peak pool neutralization and AEX loading. However, in a tandem operation (e.g., as shown in FIG. 1), precipitation may occur downstream of the 0.2 µm filter, which would be detrimental for the AEX column and/or the VRF. In addition, neutralization of the proA peak apex as it moves through the mixer is expected to produce a concentrated band of precipitated material, which may plug the filter or other downstream components. Therefore, certain steps can be introduced upstream of the proA column that would minimize the precipitation of the neutralized proA peak.

Figure 4A:
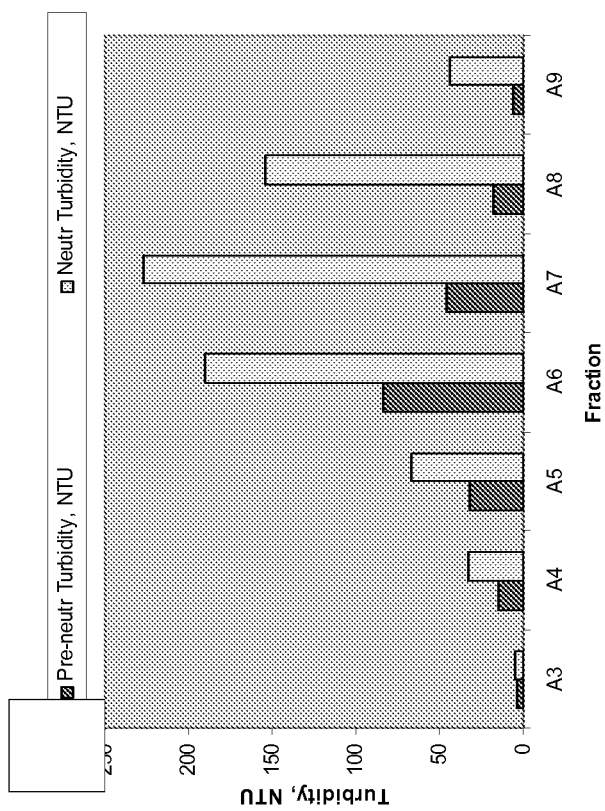
FIGS. 4A and 4B are graphs showing turbidity in proA peak fractions (~0.2 CV) pre- and post-neutralization.
Figure 4B:
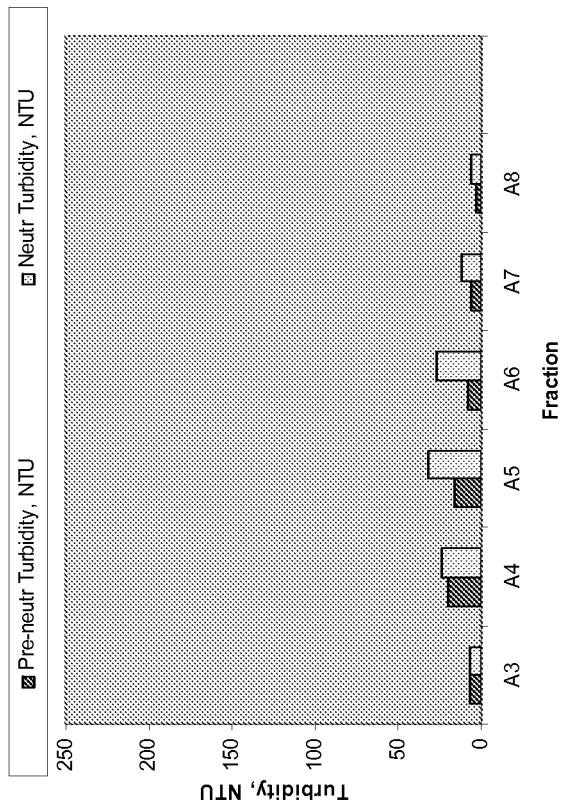

It was discovered that flocculation of conditioned media separately, or in combination with pad filtration of centrate, significantly reduced turbidity in the proA peak apex upon neutralization. Although turbidity by itself is not an accurate predictor of plugging, it serves as a convenient proxy measurement for concentration of solids. By reducing the turbidity, flocculation and pad filtration might have enabled the in-line neutralization, as it was possible to process the flocculated material without an excessive back pressure. In the experiment described below, previously pad-filtered conditioned medium was flocculated by mixing with 30 mM $CaCl_2$, 20 mM $K_2HPO_4$, 40 mM HEPES pH 7.5 for 1 hr followed by centrifugation to remove formed solids. When compared to a control, flocculated material produced much cleaner proA peak fractions (FIGS. 4A and 4B). All tandem experiments described in the present Examples used CM flocculated in this manner. Other methods of flocculation, such as using polyethyleneimine (PEI) or other flocculants can also be used. One may speculate that both flocculation and pad filtration are orthogonal methods of removal of hydrophobic conditioned medium components, such as lipids, that are prone to aggregation at high concentration and during a pH change.

Example 3

A Tandem Operation in which the proA Load is Treated with Solvent-Detergent Mixture to Inactivate Enveloped Viruses In some embodiments of tandem purification methods provided herein, low-pH hold for virus inactivation is not used, since, in some embodiments, a proA effluent is being continuously neutralized as it moves through a mixer. Therefore, a replacement step for inactivation of enveloped viruses may be necessary. The present disclosure provides that a solvent-detergent viral inactivation step can be incorporated after cell removal by centrifugation, but before passing through a proA column. Such placement of the step is beneficial because the proA is a bind-and-elute step that is capable of removing detergents in flow-through and washes. A weak partitioning AEX step is not expected to remove detergents through preferential adsorption. Removal of detergent by UF/DF step will also be inefficient, since large micelles (>70 kDa for Triton X-100) will be retained by the membrane. At the same time, detergent should not be added prior to cell removal, as it will cause cell lysis and release of viscous DNA and other impurities.

In all experiments described in the present Examples, 0.5% w/v or 0.25% w/v Triton X-100 was added to flocculated conditioned medium. The presence of detergent did not impact the performance of chromatographic steps. Concentration of Triton X-100 in the tandem peak fractions was measured by RP HPLC. Detergent was largely removed across the tandem operation: from 0.5% w/v in the load to 0.0135% w/v in the peak apex, a 1.5 log reduction.

Example 4

Tandem Operation of proA and an AEX Chromatography with Titration of the Product Stream from the proA Peak This Example describes titration of the product stream from the proA peak as it elutes from the column with a fixed volumetric ratio of a high pH solution. This brings the resulting process stream to a specific range of pH levels and salt concentration levels that promote weak partitioning chromatography on the AEX.

Weak partitioning AEX chromatography requires a precisely formulated mobile phase to accomplish retention of stronger-binding impurities, such as high-molecular weight (HMW) species and host cell proteins (HCP) at the expense of a weaker-binding product. The binding strength is determined by a thermodynamic partition coefficient, Kp, which is calculated from batch-binding experiments as the ratio of adsorbed protein concentration to free protein concentrations at equilibrium. Kp is a function of pH and concentration of anions (typically, [Cl$^-$]) in the AEX equilibration, loading and wash buffers. The Kp=f(pH, [Cl$^-$]) function is empirically derived from batch-binding experiments.

In traditional batch chromatography mode, a proA peak is eluted with a low-pH buffer, containing glycine as a buffering agent and salt (NaCl), which is a major source of chloride ions that control the binding strength to AEX downstream. The pooled peak is titrated with a concentrated neutralizing agent (high-pH Tris buffer) until the desired pH is reached. Therefore, Kp of the AEX load is controlled by accurate formulation and titration of the proA elution buffer. In a tandem arrangement such as that shown in FIG. 1, pumps A and B may be synchronized to deliver a pre-programmed variable ratio of buffers. Alternatively, Pump B may be controlled by a feedback from a pH meter after the mixer. These embodiments can generate a constant pH throughout the AEX load but may be expensive to implement and validate in a manufacturing facility.

Figure 5:
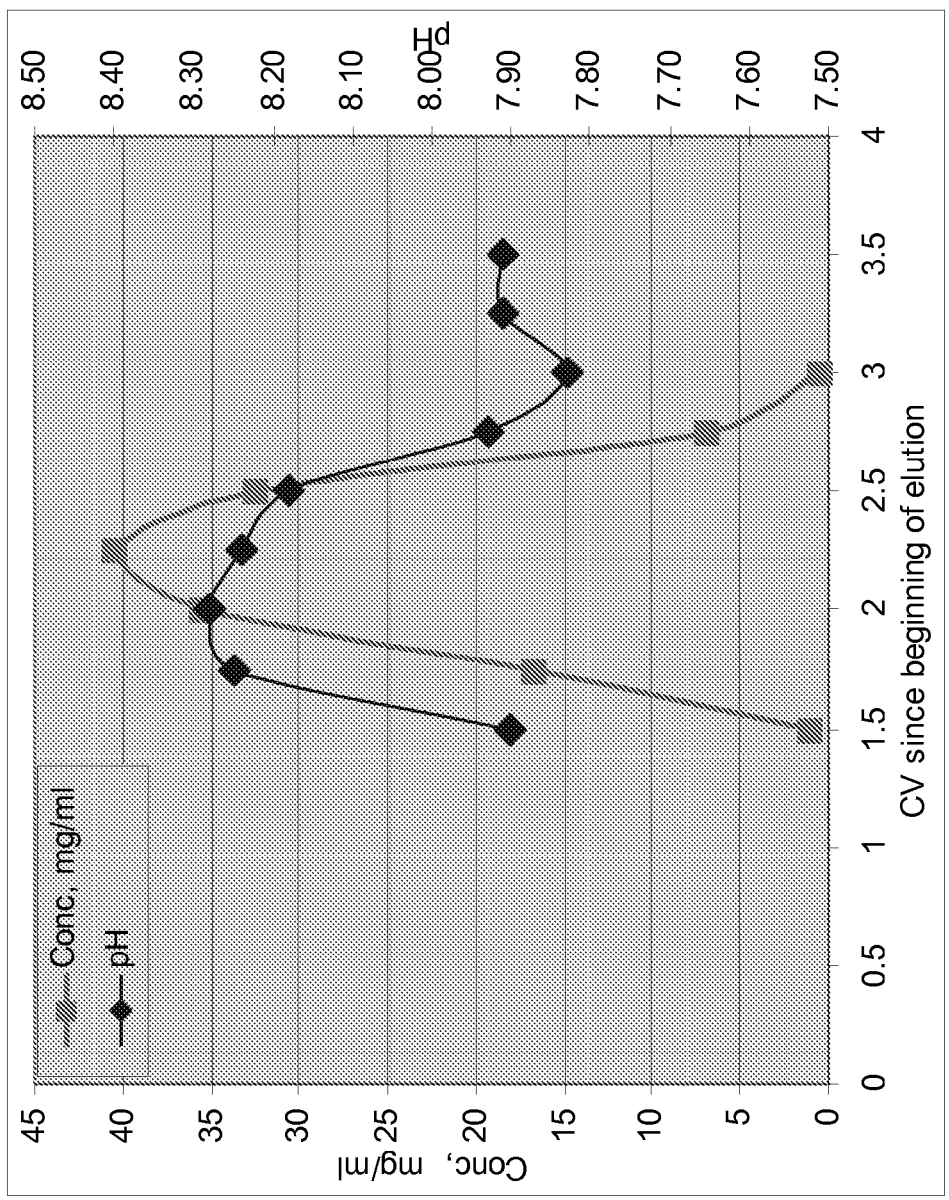
FIG. 5 is a graph showing off-line analysis of protein concentration and pH of a fractionated proA peak neutralized in-line with a constant 12% volume of titrant.

In one example of a tandem process provided by the present disclosure, pumps operate at a constant or near constant ratio of flow rates. The pH of the elution stream is variable, since high-pH final proA wash buffer is being replaced with a low pH elution buffer as it emerges from the proA column. Furthermore, both proA ligands and adsorbed product have titratable residues, which take up acid in the elution buffer. This causes the pH of the proA elution to lag behind the product peak. Thus, the composition of the proA elution stream changes from proA Wash2 buffer to the elution buffer with no buffering capacity at the leading edge of the peak to the unmodified elution buffer at the tail end of the peak. As a consequence, when the proA effluent is mixed with a constant ratio of high-pH neutralization buffer, the pH trace exhibits a pH swing. FIG. 5 is an off-line analysis of concentration and pH of a fractionated proA peak which shows this pH swing. If the pumps deliver constant flow rates, the resulting pH will change over the course of proA elution.

As shown in FIG. 5, an off-line buffer titration experiment correctly predicted that the final pH of the titrated elution buffer would stabilize at ~pH 7.9. The early fractions of the elution buffer were nearly devoid of acid and, as a consequence, became over-titrated with the neutralization buffer. The resulting pH excursion to pH 8.3 occurred during the peak apex. This pH excursion would cause a tighter binding of the affected proA peak fractions to the downstream AEX column operating in a weak partitioning mode, thereby negatively affecting the product recovery. Surprisingly, the later fractions of the elution buffer contained enough buffering capacity and thus were neutralized to the expected pH level, causing desorbtion of extra product bound earlier, and resulting in acceptable yield. The AEX column operated successfully in removing HCP and leached protein A to acceptable levels, even though the pH varied significantly. Therefore, the tandem proA/TMAE allowed the use of weak partitioning chromatography, even though the pH swung widely during the operation of the TMAE.

It was found that only the pH at the end of the proA elution determines the product quality and recovery of the tandem pool, as long as the pH consistently decreases over the course of the elution. Conversely, higher than optimal pH in the beginning of the proA elution would have minimal effect on product quality and recovery. Accordingly, in some embodiments of the present disclosure, methods are provided that include operating a tandem proA-AEX process despite the variable pH. In some embodiments, pump rates in such methods are constant.

Example 5

The Use of a Titrant that is Basic and Contains Salt for the Tandem Operation of ProA and AEX Chromatography The use of a titrant for the tandem operation of Protein A and AEX, that is both basic (pH levels about 0.5 pH units above the operation of the AEX step, and buffer concentration levels between 100 mM and 2M) and contains salt, was examined. Conditions were designed such that the addition of the titrant both increased the pH of the process intermediate and increased the ionic strength of the process intermediate in such a fashion as to maintain constant (or nearly constant) binding (as measured by such metrics as Kp, the partition coefficient) as a function of a wide range of titrant volume additions.

Figure 6A:
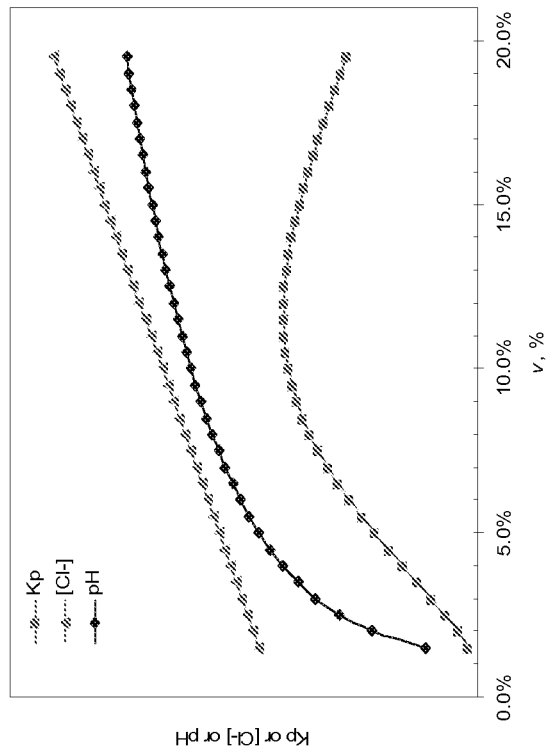
FIGS. 6A and 6B are graphs showing examples of pH, [Cl⁻] and Kp as functions of neutralization ratio (v).

In order to set the target volumetric ratio of flow rates from pumps A and B (e.g., as shown in FIG. 1), further referred to as neutralization ratio (v), the effect of v on pH and chloride concentration, [Cl$^-$], and hence on Kp, must first be determined. The pH is a function of v, pH=f(v), that can be calculated from a Henderson-Hasselbach equation and verified by titrating the elution buffer. The concentration of chloride ion as a function of v, [Cl$^-$]=f(v), could also be calculated at any ratio of buffers. The resulting pH and [Cl$^-$] functions of v can be substituted into an empirically derived function Kp=f(pH, [Cl$^-$]) and plotted as shown in FIG. 6A. The target v of operation is chosen based on desired Kp. This shape of Kp=f(v) reflects the current state of art. Therefore the combination of parameters that gives rise to this shape of the function is referred to as a Control mode of operation.

Figure 6B:
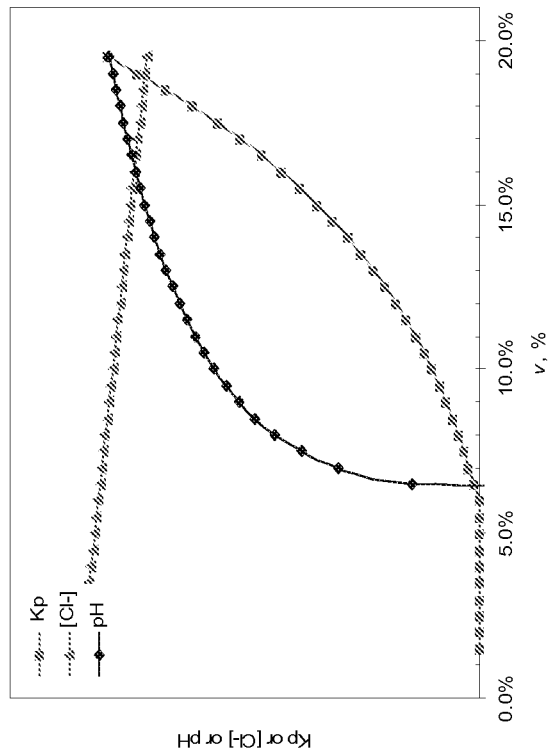

In the example shown in FIG. 6A, the low-pH proA elution buffer contains NaCl, while the neutralization buffer contains no salt. Therefore, pH rises while [Cl$^-$] drops with increasing v, resulting in steadily increasing Kp. This mode of operation presents a challenge, since it becomes critical to maintain an accurate and constant neutralization ratio in order to ensure the desired AEX performance. This accuracy may be difficult to accomplish at the manufacturing scale, since the pump performance may be variable. It was found that by incorporating salt into the neutralization buffer, one could significantly change the shape of the Kp function, as shown in FIG. 6B. This behavior of the Kp function is due to simultaneous rise in pH and [Cl$^-$] with the volume of added titrant. Higher pH makes binding to AEX stronger, while higher [Cl$^-$] has the opposite effect. The sum of these two effects produces a region of constant binding strength in a wide range of titrant addition. An inventive combination of parameters that gives rise to this shape of Kp=f(v) function is provided by the present disclosure and is referred to as Robust mode of operation. The examples shown in FIGS. 6A and 6B demonstrate that adding salt to the titrant would make the tandem process more robust with respect to accuracy of in-line buffer mixing after the proA column.

Figure 7A:
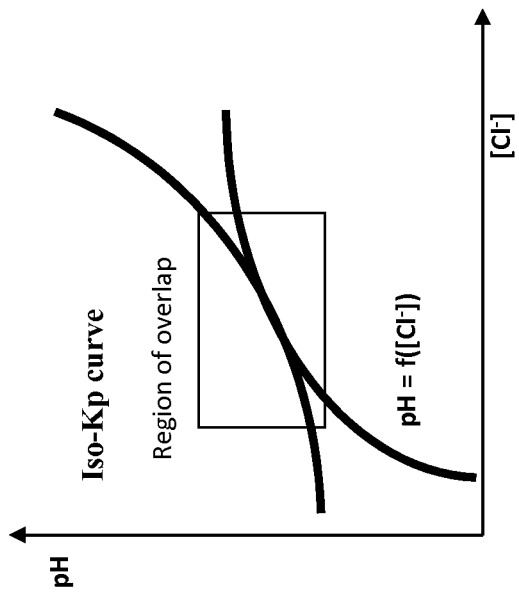
FIGS. 7A and 7B are graphs showing sketches of iso-Kp and pH=f([Cl⁻]) functions.
Figure 7B:
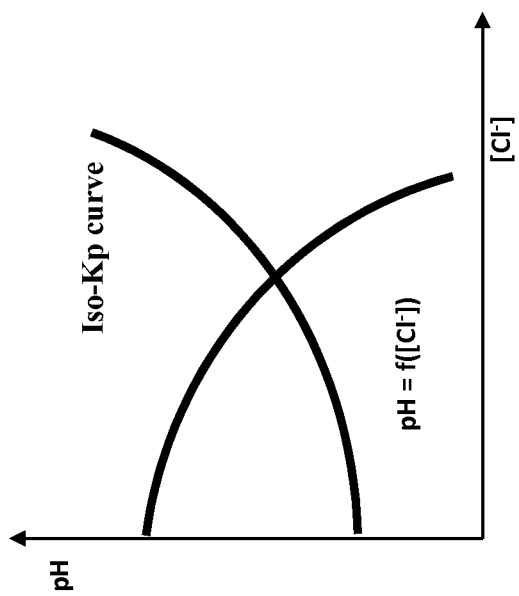

Another way of visualizing a robust tandem operation is depicted in FIG. 7. The empirical model Kp=f(pH, [Cl−]) obtained from a high-throughput batch binding experiment allows one to sketch an iso-Kp line, showing the relationship between pH and [Cl−] producing a constant binding strength. From the titration model discussed above (FIGS. 6A and 6B), pH of the neutralized proA effluent could be plotted as function of [Cl−]. According to the current state of the art, pH will be dropping with increasing [Cl−] as shown on FIG. 7A. However, when acidic proA elution buffer is titrated with a basic neutralization buffer that also contains NaCl, the chloride ion concentration in the mixture will rise linearly with v. Therefore, the pH of the titrated elution buffer plotted as a function of total [Cl−] in FIG. 7B will have the same shape as the pH function in FIG. 6B. A portion of the pH=f([Cl−]) function will overlap with an iso-Kp curve. In this region of overlap, a small variation in the % titrant volume will cause a shift along the iso-Kp line, thereby not affecting the binding strength to the AEX resin.

A clear difference between the operating modes without salt in the neutralization buffer (FIG. 6A and FIG. 7A, Control mode) and with salt (FIG. 6B and FIG. 7B, Robust mode) was demonstrated with a therapeutic MAb. Purification of this molecule by batch chromatography results in high levels of HMW in the proA pool. This HMW is effectively removed by the weak partitioning TMAE anion-exchange chromatography step. Therefore, removal of HMW was used as a marker of purity in a tandem operation.

The combination of buffers used in the simulations and experiments is summarized in Table 1. The buffer compositions were chosen in such a way as to produce the same Kp=1.25 for both modes of operation at v=11.5%. Control elution buffer compositions are very similar to the ones employed in a clinical manufacturing campaign, provided in Table 3.

TABLE 1

Buffer compositions for demonstration of robust tandem operation.

| | Elution buffer | Neutralization buffer |
|---|---|---|
| Control Mode | 49 mM Gly, 56 mM NaCl, pH 2.8 | 0.2M Tris pH 9.5 |
| Robust Mode | 50 mM Gly, 17 mM NaCl, 20 mM Tris pH 3.7 | 0.2M Tris, 0.25M NaCl pH 9.5 |

Simulations of the two modes of operation shown in FIG. 6, were verified experimentally by performing the tandem at the center point (v=11.5%), at the under-titrated point (v=6.5%) and at the over-titrated point (v=16.5%)—a total of 6 runs.

An overlay of simulated Kp functions for the Control and Robust modes is shown in FIG. 8. By definition, both modes are expected to perform similarly in terms of product purity and recovery at the center point. However, their Kp functions diverge dramatically at the two extremes of an arbitrarily chosen deviation in v. For example, at v=6.5% (equivalent to a 46.5% decrease in Pump B flow rate), the resulting Kp decreases by only 28% in the Robust mode, compared to a 91% decrease in the Control mode. Similarly, at v=16.5% (equivalent to a 52% increase in Pump B flow rate), Kp drops by only 15% in the Robust mode, but rises by 197% in the Control mode. Therefore, the model predicts relatively small changes in product quality and recovery after a ±5% absolute change in neutralization ratio in the Robust mode. However, in the Control mode, under-titration by 5% would probably cause a breakthrough of HMW and HCP, while over-titration by 5% would likely result in a product recovery loss.

Example 6

Operating a proA-AEX Tandem Step in a Range of Neutralization Ratios (v) and at Parameters that Results in a Relative Change in Kp (k) Below 100% when v is Varied from 50% to 150% of the Target In this example, tandem proA-AEX steps were conducted in a range of neutralization ratios (v) and at such combination of parameters that results in the relative change in Kp (k) below 100% when v is varied from 50% to 150% of the target. More precisely, conditions resulted in k<20%, in the range of 90% to 110% of the target v.

The operating parameters are: pH, salt concentration and pKa of the elution and neutralization buffers. Various embodiments of methods described herein provide that a robust process should operate at a target v within the robustness window. In some embodiments, a process operates at the center of the robustness window.

In order to define the robust operating window that is independent of the values of Kp and v, one can employ a function, k=ABS[Kp(v+Δv)−Kp(v−Δv)]/Kp(v), %, which measures an absolute % change in Kp within a given operating range (v±Δv).

Figure 9:
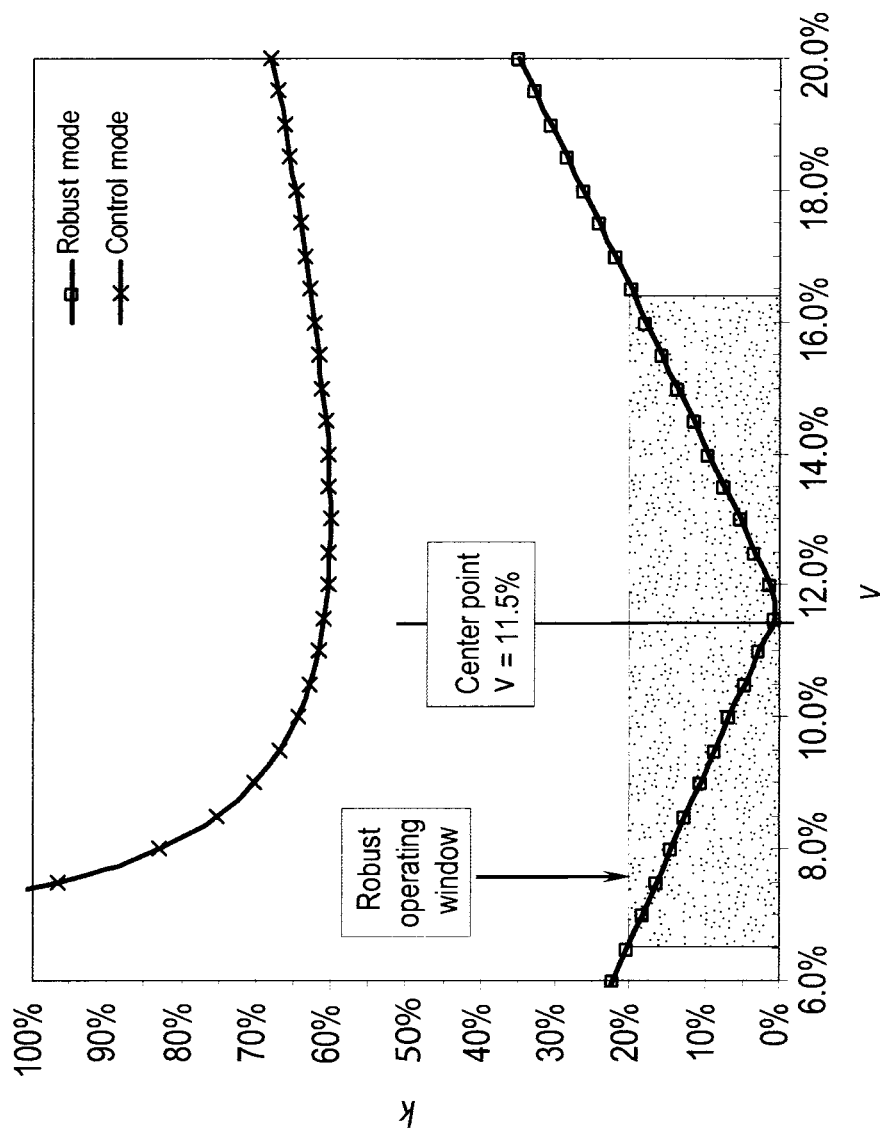
FIG. 9 is a graph showing relative Kp change function, k, for the Control (crosses) and Robust (squares) modes of tandem operation. The highlighted area shows the robust operating window.

For example, for the conditions discussed in Example 5, if Δv is set at 10%, the k function becomes:

$$k_{20}=ABS[Kp(0.9v)-Kp(1.1v)]/Kp(v),\%,$$

which is plotted in FIG. 9. The Robust operation window shown on this graph spans the range of v, where $k_{20}$ is <20%. The center point of the Robust mode of operation at v=11.5% corresponds to k=0, making it the most preferable spot to operate. In contrast, the center point of the Control mode yields k=61%. This means that by shifting from an under-titrated (by 10%) condition to an over-titrated (by 10%) condition, the Kp of the TMAE load will shift by 61% in the Control mode, while remaining constant in a Robust mode. It is predicted that operating a tandem process outside the robust operating window will significantly limit the permitted deviation in the neutralization ratio, thereby making the process more prone to failure.

For any given recipe for a tandem operation, even if the Kp function is not known, practice of the a robust mode as discussed in the Example 5 could be determined experimentally. For example, both Kp and k could be measured in a series of three batch binding experiments, where v is set at 90%, 100% and 110% of the target.

An experimental setup was based on a two-column tandem system for purification of an anti-IL-13 antibody, according to FIG. 1. It consisted of 1.1 cm×23 cm proA MabSelect column, followed by a 10 cm² 0.2 μm Sterivex filter unit, followed by a 1.6 cm×14 cm AEX TMAE column. Conditioned medium was flocculated with calcium phosphate and pad-filtered in order to minimize post-neutralization precipitation. In-line proA peak neutralization was accomplished by programming an AKTA FPLC system to deliver a certain ratio of flow from pump B in the range of 6.5%-16.5% of the total flow. The VRF unit was by-passed in this experiment. Fractions were taken post-TMAE for off-line pH and concentration measurements. HMW in the fractions was assessed by SE HPLC. HCP ELISA and leached proA ELISA were performed on pools of fractions.

Figure 10:
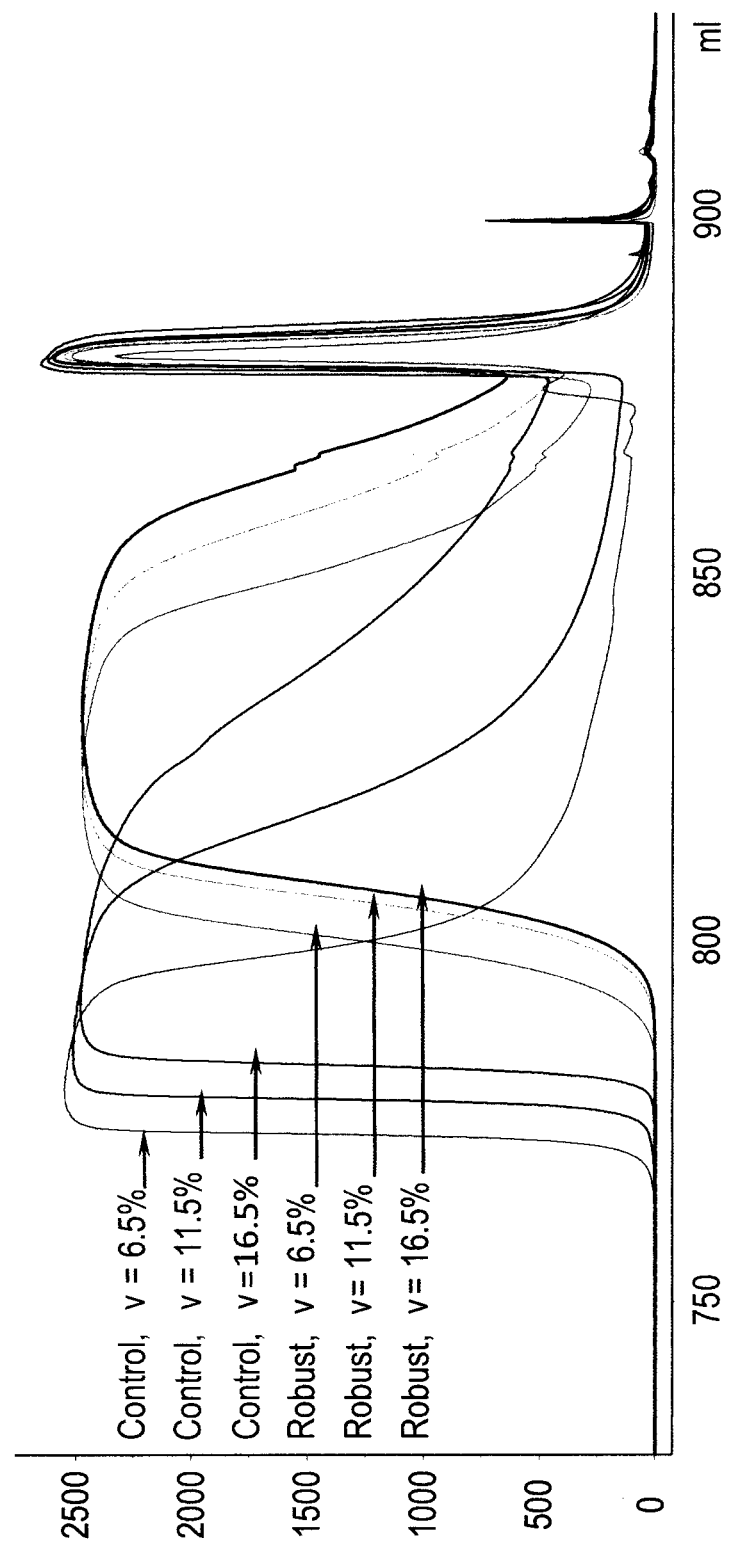
FIG. 10 is a graph showing overlaid UV traces obtained at different neutralization ratios, v, in Control and Robust neutralization modes.
Figure 11B:
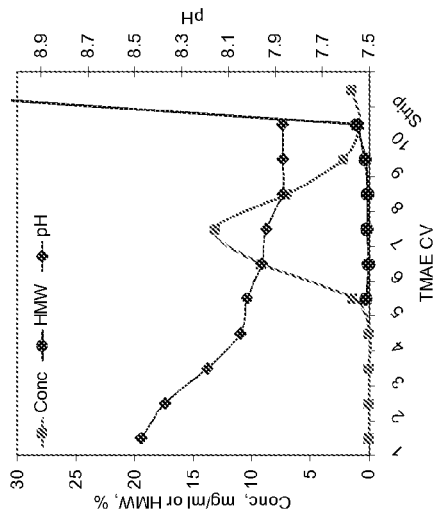
FIGS. 11A-11F are graphs showing off-line analysis of proA-TMAE tandem product collected in 1 TMAE CV fractions. Graphs are arranged as follows: left side (FIGS. 11A, 11C, 11E)—Control mode; Right side (FIGS. 11B, 11D, 11F)—Robust mode; Upper panel (FIGS. 11A, 11B)—under-titrated scenario (v=6.5%); Middle panel (FIGS. 11C, 11D)—center point (v=11.5%); Bottom panel (FIGS. 11E, 11F)—over-titrated scenario (v=16.5%)
Figure 11D:
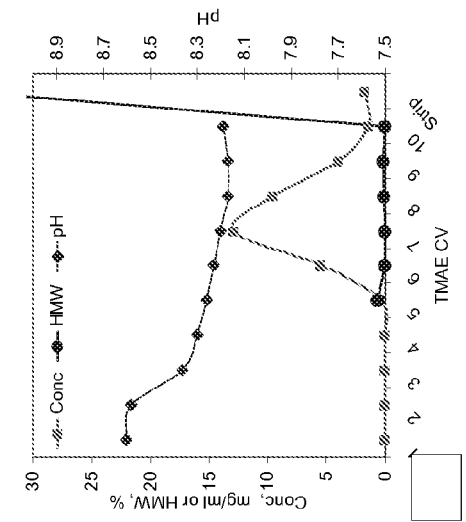
Figure 11A:
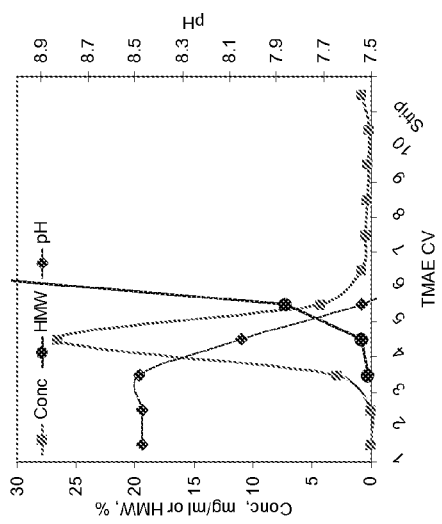
Figure 11C:
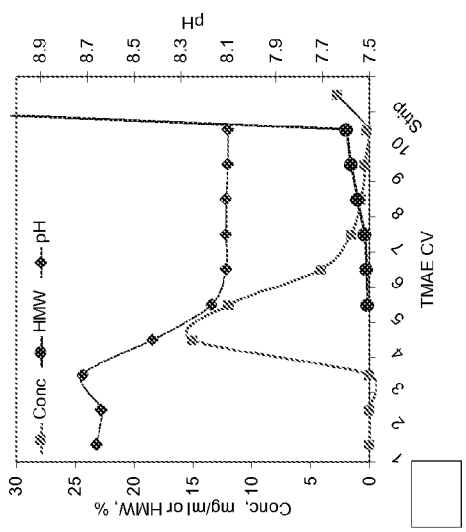
Figure 11E:
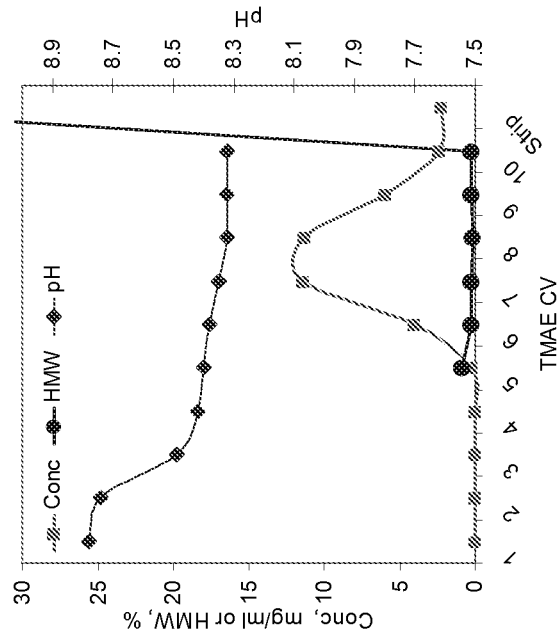
Figure 11F:
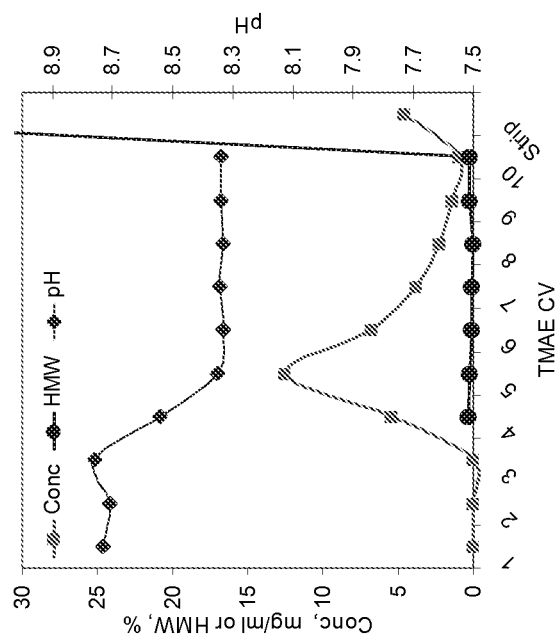

A portion of the process chromatograms showing the elution peak region is shown in FIG. 10. The order of protein breakthrough was as expected within each group representing the Control and Robust neutralization modes. The significant shift in peak retention time between the two groups was due to different pH of proA elution buffers. The Control mode employs lower pH of the elution buffer than the Robust mode (see Table 1), resulting in earlier elution from the proA column and earlier breakthrough of product through the TMAE column. The off-line measurements in post-TMAE fractions are shown in FIGS. 11A-11F. As predicted, the Robust mode of operation was not significantly affected by v. FIGS. 11B, 11D and 11F appear to have very similar pH, concentration and HMW profiles. Conversely, the Control mode exhibited definite trends in HMW breakthrough and product elution profiles as the v changes from 6.5% to 11.5% to 16.5% (FIGS. 11A, 11C and 11E). Under-titration (v=6.5%, FIG. 11A) resulted in pH levels that are too low for effective binding of product and impurities to TMAE resin. As a consequence, the product peak was very sharp and HMW broke through early in the elution. Over-titration (v=16.5%, FIG. 11E) led to the opposite result: no HMW breakthrough, but a very broad elution and low product recovery.

An earlier HMW breakthrough in the Control run at the center point (v=11.5%, FIG. 11C) might be due to a non-equilibrium effect, such as pore occlusion, caused by the inability of the TMAE resin to cope with a highly concentrated band of protein eluting from the proA column at pH=2.8.

The purity results from runs in FIG. 11 are summarized in Table 2. As predicted, the under-titrated Control run resulted in the highest levels of impurities. However, due to limited sensitivity of the assays, it was impossible to distinguish the other pools.

TABLE 2

Effect of v on the tandem pool purity in the Robust and Control modes.

| Run (as on FIG. 11) | v, % | Predicted Kp | HMW in 3CV pool, % | HCP, ppm | Leached proA, ppm |
|---|---|---|---|---|---|
| A (Control, under-titrated) | 6.5 | 0.10 | 3.26 | 30 | 4.3 |
| B (Robust, under-titrated) | 6.5 | 0.90 | 0.14 | BLOQ | BLOQ |
| C (Control, midpoint) | 11.5 | 1.25 | 0.11 | BLOQ | 0.11 |
| D (Robust, midpoint) | 11.5 | 1.25 | 0.04 | BLOQ | 0.07 |
| E Control, over-titrated) | 16.5 | 3.70 | 0.14 | BLOQ | 0.034 |
| F (Robust, over-titrated) | 16.5 | 1.06 | 0.29 | BLOQ | BLOQ |

The experimental results confirmed the prediction from the robustness model. Tandem performance was shown to be indeed more robust when salt was added to the neutralization buffer.

Example 7

Elution from Protein A

It was discovered that elution from protein A with a solution containing a buffer that has a pKa near the elution condition (usually operated at or near acidic conditions), and also a buffer that has a pKa near the operation of the subsequent AEX step (usually operated at or near neutral or basic conditions), prevented pH excursions during the neutralization of the process stream as it elutes from the protein A.

In a tandem operation with constant neutralization ratio, the leading edge of the proA elution sometimes has higher pH than the target. The elevated pH is caused by the loss of buffering capacity by the elution buffer as it passes through the loaded proA column, containing titratable proA ligands and bound product. Upon addition of high-pH neutralization buffer to the acid-depleted elution buffer, pH rises to almost the level of the neutralization buffer and stays high until all the residues on the proA column have been titrated and acid-containing elution buffer appears in the mixer.

Although usually the pH excursion occurs just before the protein front comes through the AEX and does not affect the quality or recovery of tandem pool, sometimes elevated pH is observed during the peak collection. The elevated pH means that AEX is being loaded at highly binding conditions before the neutralized elution buffer of the target pH passes through the column. In some cases, this pH excursion could cause irreversible binding of product or HMW impurities to the surface of the resin beads, resulting in pore occlusion and a premature loss of AEX binding capacity.

In order to mitigate the pH swing, 20 mM Tris-HCl was added to the elution buffer in the Robust mode, and pH-adjusted to the target pH=3.7, as listed in Table 1. Acidified Tris stayed protonated as it passed through the proA column and provided resistance to the excess of basic Tris during neutralization.

Comparison of the off-line pH measurements in tandem fractions, as shown in FIG. 11 demonstrates the effect of Tris-HCl on the extent of the pH swing. Robust neutralization runs show a shallower pH trend than the Control runs. For example, in the center point runs (v=11.5%, FIG. 11, C, D), pH decreased by only 0.1 units during the peak elution in the Robust mode, while decreasing by 0.3 units in the Control mode. In all Robust runs the pH swing is largely over when the protein concentration peaks, while in Control runs pH is still much higher than the target.

Example 8

Operation of a Batch proA Chromatography Followed by a Batch AEX Chromatography (not Tandem)

Batch proA chromatography followed by batch AEX chromatography at the conditions described in Examples 5, 6 and 7 was performed.

In a traditional batch chromatography, pH and conductivity of a neutralized proA pool are critical parameters affecting the performance of the AEX step, and hence product quality. Following the low-pH virus inactivation step, the proA peak pool is neutralized to a certain pH in order to be suitable for the weak partitioning AEX step. Batch neutralization is usually performed by gradual addition of 1-2% by volume of titrant, containing concentrated buffering agent with a pKa near the AEX run working pH. Titration proceeds until pH has reached the desired value. Conductivity is monitored and recorded, but could not be adjusted independently of pH. Ideally, both pH and conductivity reach the target values simultaneously. However, due to incomplete mixing and effect of temperature on pH measurements, the pH reading at the end of titration may be inaccurate, resulting in too much, or not enough, of the titrant being added to the pool.

In a situation of accidental over-titration, the actual pH of the neutralized pool will surpass the target by a higher degree than conductivity, since the buffering agent has only a moderate effect on conductivity. The elevated pH will cause an overall increase in Kp and a corresponding decrease in product recovery over the AEX step. For a similar reason, under-titration will result pH lower than the target, which will not be compensated by an adequate decrease in conductivity. In this case, product quality will be impacted by weaker binding of impurities.

In addition, the GMP requirement to meet two critical parameters (pH and conductivity) simultaneously without the ability to control them independently, may increase the risk of batch rejection. Therefore, it would be desirable to have a neutralization procedure with a built-in mechanism to compensate for a deviation in one parameter by automatically affecting the other in the appropriate direction. For example, if over-titration occurs with a concomitant increase in [Cl$^-$] (and conductivity), no overall change in Kp will result. Such mechanism would eliminate the necessity for having two critical parameters, since pH would be tied to conductivity, provided that the buffers are formulated accurately. Instead, the batch record may specify only the volumetric fraction of the titrant, v, to be added to the pool.

It was discovered that incorporating concentrated salt in the titrant would accomplish the effect described above. The same mathematical and physical models discussed in Examples 5 and 6 to describe continuous neutralization are applied here for a batch chromatography process. A Control mode, with no salt in the neutralization buffer and aggressive proA elution conditions is compared to a Robust mode, where neutralization buffer contains concentrated NaCl, and where proA elution occurs at relatively mild pH. Exemplary buffer compositions are summarized in Table 3. As in the tandem model, the conditions were designed to produce the same Kp=1.25 for both modes of operation at the same neutralization ratio v=1.15%.

The Control mode buffers are very similar to the ones employed in a manufacturing campaign, also listed in Table 3. The batch record specifies titration of the proA pool to pH 7.8, which would correspond to Kp=0.81 at v=1.40%.

Examples of pH, [Cl$^-$] and Kp as functions of v for a batch process shown in FIG. 13 appear to be very similar to those for a tandem process in FIG. 6. One may also notice that the neutralization buffers are exactly 10× the concentrations employed in the tandem operation, while v is exactly 0.1× of that in the tandem. This unexpected result demonstrates scalability of inventive methods provided herein: suggesting that the model for determining the robust neutralization conditions is applicable in a wide range of v.

Figure 14A:
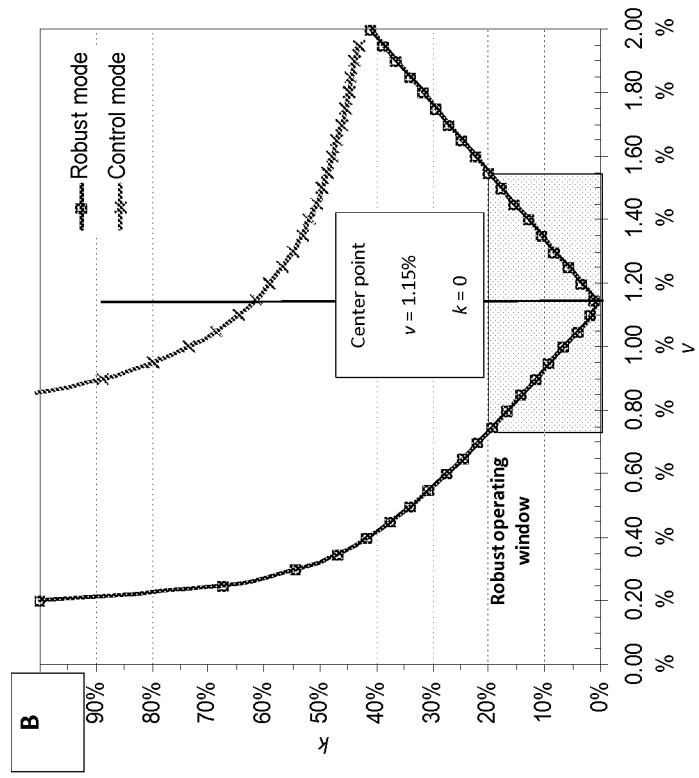
FIGS. 14A and 14B are graphs showing examples of the Control and Robust modes of batch neutralization.

FIG. 14A shows different effects an over-titration and under-titration would have on Kp=f(v) in the Robust and the Control modes of operation. For example, if titration is stopped at v=0.55% instead of the target v=1.15%, Kp in the Robust mode would be 1.09, while in the Control mode it would be reduced to 0.08, likely resulting in a failure of the TMAE step.

TABLE 3

Buffer compositions for modeling batch operation.

| | Elution Buffer | Neutralization buffer |
|---|---|---|
| Control mode | 50 mM Gly, 41.4 mM NaCl, pH 2.8 | 2M Tris pH 9.5 |

TABLE 3-continued

Buffer compositions for modeling batch operation.

| | Elution Buffer | Neutralization buffer |
|---|---|---|
| Robust Mode | 50 mM Gly, 6.8 mM NaCl, 20 mM Tris pH 3.55 | 2M Tris, 2.5M NaCl pH 9.5 |
| Used in Campaign | 50 mM Glycine 37 mM NaCl, pH 2.9 | 2M Tris, pH 8.5 |

Figure 14B:
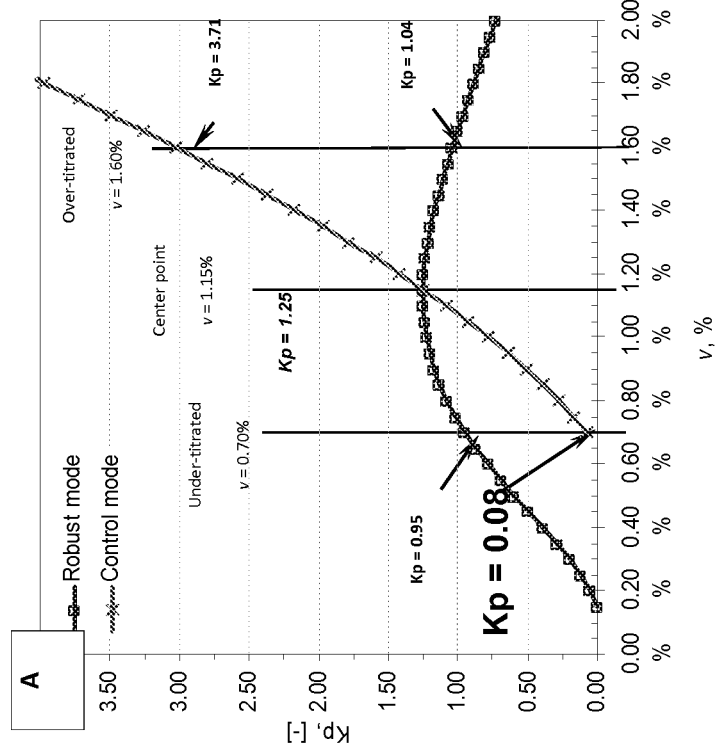

FIG. 14B defines the claimed robust window of operation, where the relative Kp change function, k=ABS[Kp(1.1v)−Kp(0.9v)]/Kp(v), % is <20%. Comparison of k behavior in the Robust and Control mode demonstrates that while it would be safe to set a titration target anywhere between 0.75% and 1.55% (but preferably, at 1.15%) of titrant addition in the Robust mode, the Control mode would produce a significant change in k in the range of ±10% deviation in v.

Example 9

Tandem Purification at Varying Binding Conditions

A small modular immunopharmaceutical was purified by control batch AEX or by tandem proA-AEX in various combinations of conditions. FIGS. 15A-15C show a comparison of these purification schemes using proA neutralization programmed to deliver weak binding conditions (Kp=1.5). One tandem process used aggressive elution (pH 3.5) without Tris in the elution buffer. The second tandem process used mild elution (pH 3.75) and Tris-HCl in the elution buffer. Adding Tris to the proA elution buffer eliminated the pH rise seen after the titration. Eluting the proA with a higher pH buffer mitigated against the purported kinetic limitation of the AEX to bind HMW1 species. Product quality was excellent.

Figure 16A:
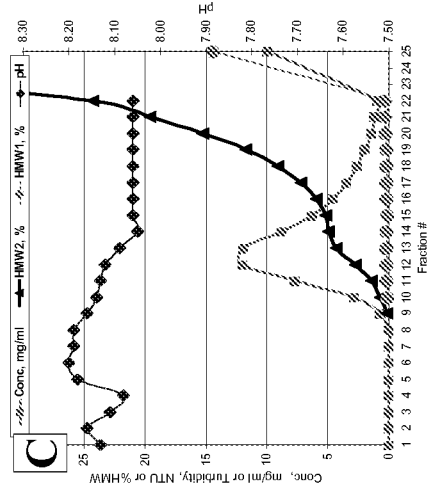
FIGS. 16A, 16B, and 16C are graphs showing a comparison processes for of purification of a small modular immunopharmaceuticals.
Figure 16B:
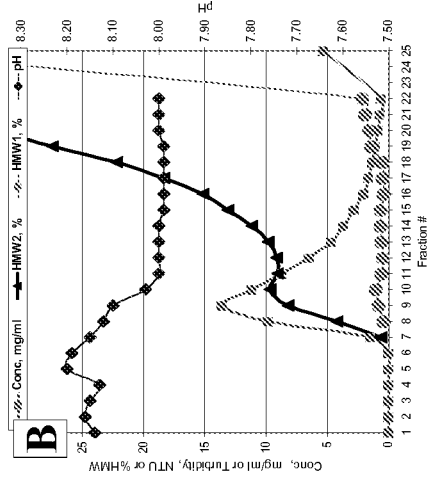
Figure 16C:
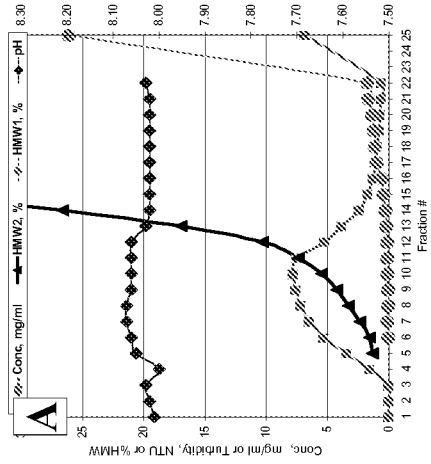

In a second set of experiments, a small modular immunopharmaceutical was also purified by control batch AEX or by tandem proA-AEX in various combinations of conditions. FIGS. 16A-16C show a comparison of these purification schemes using a proA neutralization programmed to deliver stronger binding conditions (Kp=3.0) than the first set of experiments. One tandem process used aggressive elution without Tris in the elution buffer. The second tandem process used mild elution and Tris-HCl in the elution buffer. The stronger binding conditions reduced the level of HMW1 in the aggressive elution process (FIG. 16B). Recovery was over 90% in all cases.

EQUIVALENTS

Those skilled in the art will recognize, or be able to ascertain using no more than routine experimentation, many equivalents to the specific embodiments of the present disclosure are described herein. The scope of the present disclosure is not intended to be limited to the above Description. Alternative methods and materials and additional applications will be apparent to one of skill in the art, and are intended to be included within the following claims.

We claim:

1. A method of recovering a purified protein product from a load fluid, the method comprising:
 a) providing a first column comprising a first resin, wherein the first resin comprises protein A;

b) providing a second column comprising a second resin, wherein the second resin comprises an anion exchange resin, wherein the first column is arranged in tandem with the second column;

c) exposing the load fluid comprising a protein product to the first column under conditions in which the product binds to the first resin;

d) recovering fluid comprising the product from the first resin to produce a first eluate;

e) titrating the first eluate with a titrant continuously as it passes to the second resin, wherein the titrant comprises a pH buffer and at least 150 mM of a salt, and wherein the titrant is added at a target volumetric ratio to the first eluate such that there is a change in partition coefficient of less than 20% when the actual volumetric ratio of the first eluate to the titrant varies up to about 40% from the target volumetric ratio;

f) exposing the titrated eluate to the second column under conditions in which the product binds to the second resin; and g) recovering fluid comprising the product from the second resin to produce a second eluate, thereby recovering the purified protein product from the load fluid.

2. The method of claim 1, wherein the first eluate is titrated with the titrant in a volumetric ratio of between about 95:5 to 80:20.

3. The method of claim 1, wherein a first pump delivers the load fluid to the first resin, a second pump delivers the titrant to the first eluate, and wherein the pumps are operated at a ratio of flow rates that varies by less than 30%.

4. The method of claim 1, wherein the titrant and first eluate are passed through a mixer, prior to exposure to the second resin.

5. The method of claim 1, wherein the method comprises detecting pH of the titrated eluate, prior to exposure to the second resin.

6. The method of claim 1, wherein the titrated eluate is passed through a filter, prior to exposure to the second resin.

7. The method of claim 1, wherein solids are removed from the load fluid by precipitation.

8. The method of claim 1, wherein the load fluid comprises cell culture medium.

9. The method of claim 1, wherein the protein comprises an antigen-binding portion of an antibody.

10. The method of claim 1, wherein the first resin selectively binds immunoglobulins.

11. The method of claim 1, wherein the titrant alters one or more conditions of the first eluate such that product in the titrated eluate binds to the second resin in a weak partitioning mode.

12. The method of claim 11, wherein the conditions of the titrated eluate and the resin are such that the partition coefficient of the product for the resin is 0.1-20.

13. The method of claim 1, wherein the titrant has a pH which is 0.5 pH units above a pH at which the anion exchange resin binds to product in the titrated eluate in a weak partitioning mode.

14. The method of claim 1, wherein the titrant increases ionic strength of the eluate of the first resin such that the product maintains binding to the second resin over a range of titrant volume additions.

15. The method of claim 1, wherein the method comprises treating the load fluid, the first eluate, or the second eluate with one or more virus reduction treatments.

16. The method of claim 1, wherein the method comprises treating the load fluid, the first eluate, or the second eluate with one or more viscosity reducing treatments.

17. The method of claim 1, wherein the second resin is an anion exchange resin, and wherein the product is recovered from the first resin in a fluid comprising a buffer which has a pKa that is near conditions under which the product elutes from the resin and a buffer having a pKa near conditions under which the product binds to the second resin in a weak partitioning mode.

* * * * *